US011357718B2

(12) United States Patent
Chiattello et al.

(10) Patent No.: US 11,357,718 B2
(45) Date of Patent: Jun. 14, 2022

(54) POLYMER-BASED ANTIMICROBIAL COMPOSITIONS AND METHODS OF USE THEREOF

(71) Applicant: eXion labs Inc., West Des Moines, IA (US)

(72) Inventors: Marion L. Chiattello, Cedar Falls, IA (US); Mark Oman, West Des Moines, IA (US)

(73) Assignee: eXion labs Inc., West Des Moines, IA (US)

( * ) Notice: Subject to any disclaimer, the term of this patent is extended or adjusted under 35 U.S.C. 154(b) by 0 days.

(21) Appl. No.: 16/121,023

(22) Filed: Sep. 4, 2018

(65) Prior Publication Data

US 2019/0000745 A1  Jan. 3, 2019

Related U.S. Application Data

(62) Division of application No. 15/662,119, filed on Jul. 27, 2017.

(60) Provisional application No. 62/488,421, filed on Apr. 21, 2017, provisional application No. 62/368,008, filed on Jul. 28, 2016.

(51) Int. Cl.

| | | |
|---|---|---|
| *A61K 8/84* | (2006.01) | |
| *A01N 25/08* | (2006.01) | |
| *A61Q 17/00* | (2006.01) | |
| *A01N 33/12* | (2006.01) | |
| *A61K 8/81* | (2006.01) | |
| *A01N 43/36* | (2006.01) | |
| *A01N 25/32* | (2006.01) | |
| *A01N 25/24* | (2006.01) | |
| *A01N 59/16* | (2006.01) | |
| *A01N 25/22* | (2006.01) | |
| *A61K 8/365* | (2006.01) | |
| *C08L 39/00* | (2006.01) | |
| *C09D 5/14* | (2006.01) | |
| *C09D 139/00* | (2006.01) | |
| *A61K 8/29* | (2006.01) | |
| *A01N 25/34* | (2006.01) | |

(52) U.S. Cl.
CPC ............... *A61K 8/84* (2013.01); *A01N 25/08* (2013.01); *A01N 25/22* (2013.01); *A01N 25/24* (2013.01); *A01N 25/32* (2013.01); *A01N 25/34* (2013.01); *A01N 33/12* (2013.01); *A01N 43/36* (2013.01); *A01N 59/16* (2013.01); *A61K 8/29* (2013.01); *A61K 8/365* (2013.01); *A61K 8/817* (2013.01); *A61K 8/8158* (2013.01); *A61Q 17/005* (2013.01); *C08L 39/00* (2013.01); *C09D 5/14* (2013.01); *C09D 139/00* (2013.01); *A61K 2800/5424* (2013.01); *A61K 2800/5426* (2013.01); *A61K 2800/594* (2013.01); *C08L 2203/02* (2013.01); *C08L 2205/03* (2013.01)

(58) Field of Classification Search
CPC ........ A01N 25/08; A01N 25/22; A01N 25/24; A01N 25/32; A01N 25/34; A01N 33/12; A01N 43/36; A01N 59/16; A61K 8/29; A61K 8/365; A61K 8/8158; A61K 8/817; A61K 8/84; A61Q 17/005; C08L 39/00; C09D 139/00; C09D 5/14
See application file for complete search history.

(56) References Cited

U.S. PATENT DOCUMENTS

| | | | | |
|---|---|---|---|---|
| 3,318,816 | A | * | 5/1967 | Trowbridge .............. C11D 1/22 510/357 |
| 3,909,469 | A | * | 9/1975 | Miller ..................... C08L 79/02 524/44 |
| 4,251,596 | A | | 2/1981 | de Montigny et al. |
| 4,402,937 | A | | 9/1983 | Denzinger et al. |
| 4,551,512 | A | | 11/1985 | Straub et al. |
| 4,600,789 | A | | 7/1986 | Sugerman et al. |
| 4,614,762 | A | | 9/1986 | Marans et al. |
| 4,668,747 | A | | 5/1987 | Cadel et al. |

(Continued)

FOREIGN PATENT DOCUMENTS

| | | |
|---|---|---|
| CN | 100372599 C | 3/2008 |
| CN | 101189041 A | 5/2008 |

(Continued)

OTHER PUBLICATIONS

Thimerosal Article Ency. Britannica, p. 1, (Year: Nov. 20, 2018).*
Tebu-bio blog (PEI Transfection patents, (Year: Feb. 7, 2015).*
Brodkorb et al., "Development of a New Monomer for the Synthesis of Intrinsic Antimicrobial Polymers with Enhanced Material Properties," *Int. J. Mol. Sci.*, 16: 20050-20066 (2015).
Carmona-Ribeiro et al., "Cationic Antimicrobial Polymers and Their Assemblies," *Int. J. Mol. Sci.*, 14: 9906-9946 (2013).
Curtis et al., "Unusual Salt and pH Induced Changes in Polyethylenimine Solutions," *Plos-One*, 11(9): 1-20 (Sep. 29, 2016).

(Continued)

*Primary Examiner* — Matthew P Coughlin
*Assistant Examiner* — Thurman Wheeler
(74) *Attorney, Agent, or Firm* — Leydig, Voit & Mayer, Ltd.

(57) ABSTRACT

Provided is a polymer-based antimicrobial composition that is non-toxic, water soluble, and that mitigates the transmission of infectious diseases from surfaces. The composition comprises a cationic polymer, at least one adhesion promoter, optionally organic and/or inorganic particles that are photocatalytically active in visible light, and a carrier, in which the components of the composition are not covalently bound to one another. Also provided is an antimicrobial composition that comprises at least (i) a polyethylenimine-based polymer and a carrier or (ii) an organic and/or inorganic particle that is photocatalytically active in visible light, an adhesion promoter, and a carrier. The antimicrobial compositions can be applied to disinfect a surface and to form residual self-sanitizing films on the surface that are removable.

28 Claims, 1 Drawing Sheet

(56) References Cited

U.S. PATENT DOCUMENTS

| | | | |
|---|---|---|---|
| 4,692,494 A | 9/1987 | Sonenstein | |
| 4,835,206 A | 5/1989 | Farrar et al. | |
| 5,061,485 A | 10/1991 | Oakes et al. | |
| 5,578,598 A | 11/1996 | Abe et al. | |
| 5,932,458 A | 8/1999 | Piazza, Jr. et al. | |
| 6,001,920 A * | 12/1999 | Ghafoor | C02F 1/56 524/500 |
| 6,017,561 A * | 1/2000 | Zhou | A01N 33/12 424/486 |
| 6,018,063 A | 1/2000 | Isbell et al. | |
| 6,080,417 A | 6/2000 | Kramer et al. | |
| 6,270,754 B1 | 8/2001 | Zhou et al. | |
| 6,897,168 B2 | 5/2005 | Branham et al. | |
| 6,905,814 B1 | 6/2005 | Aubay et al. | |
| 6,960,371 B2 | 11/2005 | Bunyard et al. | |
| 7,244,797 B2 | 7/2007 | Kurihara et al. | |
| 7,709,694 B2 | 5/2010 | Batich et al. | |
| 7,896,168 B2 | 3/2011 | Collias et al. | |
| 8,071,255 B2 | 12/2011 | Schlenoff | |
| 8,106,111 B2 | 1/2012 | McCaulley et al. | |
| 8,323,633 B2 | 12/2012 | Snyder et al. | |
| 8,404,779 B2 | 3/2013 | Chenault | |
| 8,545,898 B2 | 10/2013 | Fukuda et al. | |
| 8,697,790 B2 | 4/2014 | Polverari et al. | |
| 8,975,220 B1 | 3/2015 | Kaur et al. | |
| 9,005,662 B2 | 4/2015 | Schlenoff | |
| 9,127,173 B2 | 9/2015 | Lee et al. | |
| 9,212,286 B2 | 12/2015 | Whiteford et al. | |
| 9,399,044 B2 | 7/2016 | Cheng et al. | |
| 9,587,353 B2 | 3/2017 | Jogikalmath et al. | |
| 2003/0207121 A1 | 11/2003 | McGee | |
| 2005/0249791 A1 | 11/2005 | Hobbs et al. | |
| 2006/0269493 A1 | 11/2006 | Toreki | |
| 2007/0048344 A1 * | 3/2007 | Yahiaoui | C08K 5/0058 424/405 |
| 2007/0128121 A1 | 6/2007 | Densmore et al. | |
| 2007/0202177 A1 * | 8/2007 | Hoang | A01N 31/02 424/486 |
| 2008/0021212 A1 * | 1/2008 | Whiteford | A01N 43/90 540/472 |
| 2008/0039547 A1 | 2/2008 | Khatri et al. | |
| 2008/0085949 A1 * | 4/2008 | McGhee | C08G 18/10 523/149 |
| 2008/0206293 A1 | 8/2008 | Toreki et al. | |
| 2008/0213394 A1 | 9/2008 | Tullo et al. | |
| 2009/0206038 A1 * | 8/2009 | Thomas | A61L 33/06 210/639 |
| 2010/0291169 A1 * | 11/2010 | Toreki | A61F 13/00063 424/405 |
| 2011/0060070 A1 | 3/2011 | Dias | |
| 2011/0200655 A1 | 8/2011 | Black et al. | |
| 2011/0236450 A1 | 9/2011 | Scheuing et al. | |
| 2011/0244256 A1 | 10/2011 | Song et al. | |
| 2012/0107726 A1 | 5/2012 | Ogata et al. | |
| 2012/0141396 A1 | 6/2012 | Toreki et al. | |
| 2013/0036558 A1 | 2/2013 | Locklin | |
| 2013/0165525 A1 | 6/2013 | Scheuing et al. | |
| 2013/0183516 A1 | 7/2013 | Krogman et al. | |
| 2013/0209811 A1 | 8/2013 | Dams et al. | |
| 2014/0294749 A1 | 10/2014 | Gentle et al. | |
| 2014/0369953 A1 | 12/2014 | Purschwitz et al. | |
| 2015/0038400 A1 | 2/2015 | Vail | |
| 2015/0119353 A1 | 4/2015 | Vail | |
| 2015/0252190 A1 | 9/2015 | Rodgers et al. | |
| 2015/0283301 A1 | 10/2015 | Semetey et al. | |
| 2016/0032143 A1 | 2/2016 | Wolbers et al. | |
| 2016/0143275 A1 | 5/2016 | Lan et al. | |
| 2016/0262383 A1 | 9/2016 | Lan et al. | |

FOREIGN PATENT DOCUMENTS

| | | |
|---|---|---|
| CN | 102131527 A | 7/2011 |
| CN | 102258064 A | 11/2011 |
| CN | 102405063 A | 4/2012 |
| CN | 103167798 A | 6/2013 |
| CN | 101669518 B | 8/2013 |
| CN | 103333571 A | 10/2013 |
| CN | 104436265 A | 3/2015 |
| CN | 105273443 A | 1/2016 |
| CN | 105901015 A | 8/2016 |
| CN | 106189304 A | 12/2016 |
| DE | 10211561 A1 | 10/2003 |
| EP | 1450966 A2 | 9/2004 |
| EP | 1539827 A1 | 6/2005 |
| EP | 1686993 A2 | 8/2006 |
| EP | 2034831 A2 | 3/2009 |
| EP | 2385105 A2 | 11/2011 |
| EP | 2817013 A2 | 12/2014 |
| JP | H08-165208 A | 6/1996 |
| JP | H08-165214 A | 6/1996 |
| JP | H08-165215 A | 6/1996 |
| JP | 2000-070728 A | 3/2000 |
| JP | 2004-346291 A | 12/2004 |
| JP | 2006-151907 A | 6/2006 |
| JP | 2009-263820 A | 11/2009 |
| RU | 2524635 C2 | 7/2014 |
| WO | WO 2003/039602 A2 | 5/2003 |
| WO | WO 2004/018524 A1 | 3/2004 |
| WO | WO 2005/046738 A2 | 5/2005 |
| WO | WO 2007/142967 A2 | 12/2007 |
| WO | WO 2010/096595 A2 | 8/2010 |
| WO | WO 2011/123297 A1 | 10/2011 |
| WO | WO 2012/004364 A1 | 1/2012 |
| WO | WO 2013/054860 A1 | 4/2013 |
| WO | WO 2013/126550 A2 | 8/2013 |
| WO | WO 2015/034357 A1 | 3/2015 |
| WO | WO 2016/086012 A1 | 6/2016 |
| WO | WO 2016/086014 A1 | 6/2016 |

OTHER PUBLICATIONS

Dalai et al., "A comparative cytotoxicity study of $TiO_2$ Nanoparticles under Light and Dark Conditions at Low Exposure Concentrations," *Toxicol. Res.*, 1(2): 116-130 (2012).

Dargan et al., "Positively Charged Polyvinyl Acetate Emulsions—Their Preparation And Properties," *Br. Polym. J.*, 2: 174-177 (1970).

de la Rosa et al., "Fast and accurate partial hydrolysis of poly(2-ethyl-2-oxazoline) into tailored linear polyethylenimine copolymers," *Polym. Chem.*, 5: 4957-4964 (2014).

Dobrynin et al., "Cascade of Transitions of Polyelectrolytes in Poor Solvents," *Macromolecules*, 29: 2974-2979 (1996).

Dunlop et al., "Inactivation of clinically relevant pathogens by photocatalytic coatings," *J. Photochem. Photobiol. A: Chem.*, 216: 303-310 (2010).

Farouk et al., "ZnO Nanoparticles-Chitosan Composite as Antibacterial Finish for Textiles," *International Journal of Carbohydrate Chemistry*, 8 pages (2012).

Fleischer et al., "Transforming polyethylenimine into a pH-switchable hydrogel by additional supramolecular interactions," *Chem. Commun.*, 50: 10464-10467 (2014).

Gibney et al., "Poly(ethylene imine)s as Antimicrobial Agents with Selective Activity," *Macromolecolar Bioscience*, 11 pages (2012).

Giron-Gonzalez et al., "Polyelectrolyte Complexes of Low Molecular Weight PEI and Citric Acid as Efficient and Nontoxic Vectors for in Vitro and in Vivo Gene Delivery," *Bioconjogate Chem.*, 27: 549-561 (Feb. 3, 2016).

Green et al., "Immobilized Antimicrobial Agents: A Critical Perspective," *Science Against Microbial Pathogens: Communicating Current Research and Technological Advances*, A. Méndez-Vilas (Ed.), Formatex Research Center, Spain, 84-98 (2011).

Gruškiene et al., "Quaternization of chitosan and partial destruction of the quaternized derivatives making them suitable for electrospinning," *CHEMIJA*, 24(4): 325-334 (2013).

Guo et al., "Polymer/nanosilver composite coatings for antibacterial applications," *Colloids Surfaces A. Physicochem. Eng. Aspects*, 439: 69-83 (2013).

Haldar et al., "Polymeric coatings that inactivate both influenza virus and pathogenic bacteria," *Pro. Nat. Acad. Sci.* 103(47): 17667-17671 (2006).

(56) References Cited

OTHER PUBLICATIONS

Hoque et al., "Broad Spectrum Antibacterial and Antifungal Polymeric Paint Materials: Synthesis, Structure-Activity Relationship, and Membrane-Active Mode of Action," *ACS Appl. Mater. Interfaces*, 7: 1804-1815 (2015).
Horvath, "Appropriate Conditions for Polyelectrolyte Titration to Determine the Charge of Cellulosic Fibers," *Royal Institute of Technology*, 39 pages (2003).
Isemura et al., "The Dissolution of Water-Insoluble Polymers in the Surfactant Solution. The Polyelectrolyte-Like Behavior of the Dissolved Polymers," *J. Poly. Sci.*, 33: 337-352 (1958).
Jasmeet et al., "Interpolyelectrolyte Complexes as Prospective Carriers for Controlled Drug Delivery," *Int. Res. J. Pharm.*, 3(4): 58-62 (2012).
Jeong et al., "DNA transfection using linear poly(ethylenimine) prepared by controlled acid hydrolysis of poly(2-ethyl-2-oxazoline)," *Journal of Controlled Release*, 73: 391-399 (2001).
Johal et al., "Polymer-surfactant complexation in polyelectrolyte multilayer assemblies," *Soft Matter* 3: 34-46 (2007).
Kawabata et al., "Adsorption of Bacteriophage T4 by Cross-linked Poly(vinylpyridinium halide)," *Agriculture and Biological Chemistry*, 50(6): 1551-1555 (1986).
Kenawy et al., "Biologically Active Polymers. V. Synthesis and Antimicrobial Activity of Modified Poly(glycidyl methacrylate-co-2-hydroxyethyl methacrylate) Derivatives with Quaternary Ammonium and Phosphonium Salts," *J. Poly. Sci. A: Polymer Chemistry*, 40: 2384-2393 (2002).
Kickelbick, "Concepts for the incorporation of inorganic building blocks into organic polymers on a nanoscale," *Prog. Polym. Sci.*, 28: 83-114 (2003).
Kim et al., "Polyelectrolyte complex composite gel membranes based on two cationic polymers for the separation of methyl tert-butyl ether and methanol mixtures," *Current Applied Physics*, 9: e47-e50 (2009).
Kim et al., "Complexation and coacervation of like-charged polyelectrolytes inspired by mussels," *Proc. Natl. Acad. Sci. USA*, 113(7): E847-E853 (Feb. 16, 2016).
Kriz et al., "Competitive/Cooperative Electrostatic Interactions in Macromolecular Complexes: Multinuclear NMR Study of PDADMAC-PMANa Complexes in the Presence of $Al^{3+}$ Ions," *Langmuir*, 18: 9594-9599 (2002).
Kügler et al., "Evidence of a charge-density threshold for optimum efficiency of biocidal cationic surfaces," *Microbiology*, 151: 1341-1348 (2005).
Lankalapalli et al., "Polyelectrolyte Complexes: A Review of their Applicability in Drug Delivery Technology," *Indian J. Pharm. Sci.*, 71(5): 481-487 (2009).
Lee et al., "Polymer Adhesion vs Substrate Receptor Group Density," *Macromolecules*, 33: 2680-2687 (2000).
Lee et al., "Conjugated polyelectrolytes: A new class of semiconducting material for organic electronic devices," *Polymer*, 54: 5104-5121 (2013).
Léger et al., "Adhesion mechanisms at soft polymer interfaces," *Phil. Trans. R. Soc. A*, 366: 1425-1442 (2008).
Li et al., "Synthesis of Water-Soluble Cationic Polymers with Star-Like Structure Based on Cyclodextrin Core via ATRP," *Journal of Polymer Science: Part A: Polymer Chemistry*, 43: 6345-6354 (2005).
Lighter et al., "Design of Antibacterial Surfaces and Interfaces: Polyelectrolyte Multilayers as a Multifunctional Platform," *Macromolecules*, 42: 8573-8586 (2009).
Lim et al., "The inhibition of prions through blocking prion conversion by permanently charged branched polyamines of low cytotoxicity," *Biomaterials*, 31: 2025-2033 (2010).
Liu et al., "Why do Some Immobilized N-Alkylated Polyethylenimines Far Surpass Others in Inactivating Influenza Viruses?," *Biomacromolecules*, 16: 351-356 (2015).
Liufu et al., "Adsorption of poly(acrylic acid) onto the surface of titanium dioxide and the colloidal stability of aqueous suspension," *Journal of Colloid and Interface Science*, 281: 155-163 (2005).

Luo et al., "Recent development of chitosan-based polyelectrolyte complexes with natural polysaccharides for drug delivery," *International Journal of Biological Macromolecules*, 64: 353-367 (2014).
Mikhaylova et al., "Preclinical Evaluation of Antimicrobial Efficacy and Biocompatibility of a Novel Bacterial Barrier Dressing," *Wounds*, 23(2): 24-31 (2011).
Miller-Chou et al., "A review of polymer dissolution," *Prog. Polym. Sci.*, 28: 1223-1270 (2003).
Moiz et al., "Bimodal Dispersion of Silver Nanoparticles for Conducting Polymer," *4th International Conference on Intelligent and Advanced Systems*, 814-819 (2012).
Mukherji et al., "Polymer collapse in miscible good solvents is a generic phenomenon driven by preferential adsorption," *Nature Communications*, 5(4882): 1-6 (2014).
Munoz-Bonilla et al., "Polymeric materials with antimicrobial activity," *Progress in Polymer Science*, 37: 281-339 (2012).
Murata et al., "Permanent, non-leaching antibacterial surfaces—2: How high density cationic surfaces kill bacterial cells," *Biomaterials*, 11 pages (2007).
Noriega et al., "A general relationship between disorder, aggregation and charge transport in conjugated polymers," *Nature Materials*, 12: 1038-1044 (2013).
Ouyang et al., "Monomodal Polyelectrolyte Complex Nanoparticles of PDADMAC/Poly(styrenesulfonate): Preparation and Protein Interaction," *Macromol. Biosci.*, 6: 929-941 (2006).
"Polyelectrolyte Adsorption"—Wikipedia, This page was last modified on Apr. 10, 2016, at 18:03. Retrieved from https://en.wikipedia.org/w/index.php?title=Polyelectrolyte_adsorption&oldid=714590340, Accessed Apr. 29, 2017.
Poptoshev et al., "Forces between Glass Surfaces in Aqueous Polyethylenimine Solutions," *Langmuir*, 18: 2590-2594 (2002).
Priftis et al., "Ternary, Tunable Polyelectrolyte Complex Fluids Driven by Complex Coacervation," *Macromolecules*, 47: 3076-3085 (2014).
Prime et al., "Duolayers at Air/Water Interface: Improved Lifetime through Ionic Interactions," *J. Phys. Chem. B*, 120(30): 7401-7407 (Jul. 15, 2016).
"Protocol for Residual Self-Sanitizing Activity of Dried Chemical Residues on Hard Nonporous Surfaces," *Protocol #01-1A*, Retrieved from https://www.epa.gov/home/pdf-files, Downloaded Sep. 26, 2017.
Roest et al., "Charge properties and bacterial contact-killing of hyperbranched polyurea-polyethyleneimine coatings with various degrees of alkylation," *Applied Surface Science*, 356: 325-332 (2015).
Rojas et al., "Effect of Polyelectrolyte Charge Density on the Adsorption and Desorption Behavior on Mica," *Langmuir*, 18: 1604-1612 (2002).
Rossegger et al., "Design Strategies for Functionalized Poly(2-oxazoline)s and Derived Materials," *Polymers*, 5: 956-1011 (2013).
Shi et al., "Titanium dioxide nanoparticles: a review of current toxicological data," *Particle and Fibre Toxicology*, 10(15): 1-33 (2013).
Siedenbiedel et al., "Antimicrobial Polymers in Solution and on Surfaces: Overview and Functional Principles," *Polymers*, 4: 46-71 (2012).
Simoncic et al., "Structures of Novel Antimicrobial Agents for Textiles—A Review," *Textile Research Journal*, 80(16): 1721-1737 (2010).
Strassburg et al., "Nontoxic, Hydrophilic Cationic Polymers-Identified as Class of Antimicrobial Polymers," *Macromolecular Bioscience*, 15: 1710-1723 (2015).
Tan et al., "Quaternized Chitosan as an Antimicrobial Agent: Antimicrobial Activity, Mechanism of Action and Biomedical Applications in Orthopedics," *Int. J. Mol. Sci.*, 14: 1854-1869 (2013).
Tauhardt et al., "Linear Polyethyleneimine: Optimized Synthesis and Characterization—On the Way to 'Pharmagrade' Batches," *Macromolecular Chemistry and Physics*, 212: 1918-1924 (2011).
Tejero et al., "High Efficiency Antimicrobial Thiazolium and Triazolium Side-Chain Polymethacrylates Obtained by Controlled Alkylation of the Corresponding Azole Derivatives," *Biomacromolecules*, 16: 1844-1854 (2015).

(56) References Cited

OTHER PUBLICATIONS

Timofeeva et al., "Antimicrobial polymers: mechanism of action, factors of activity, and applications," *Appl. Microbiol. Biotechnol.*, 18 pages (2010).
Uppu et al., "Polymers with tunable side-chain amphiphilicity as non-hemolytic antibacterial agents," *Chem. Commun.*, 49: 9389-9391 (2013).
Uppu et al., "Polymers with tunable side-chain amphiphilicity as non-hemolytic antibacterial agents," *Chem. Commun.*, Supporting information, 24 pages (2013).
Valade et al., "Preparation of Solid Alkaline Fuel Cell Binders Based on Fluorinated Poly(diallyldimethylammonium chloride)s [Poly(DADMAC)] or Poly(chlorotrifluoroethylene-co-DADMAC) Copolymers," *Journal of Polymer Science: Part A: Polymer Chemistry*, 47:2043-2058 (2009).
Yudovin-Farber et al., "Quaternary Ammonium Polyethyleneimine: Antibacterial Activity," *Journal of Nanomaterials*, 2010: 8 pages (2010).
Zander et al., "Charge Density Quantification and Antimicrobial Efficacy," *Army Research Laboratory*, ARL-TR-4530, 20 pages (2008).
Zhu et al., "Layer-by-layer assemblies for antibacterial applications," *Biomater. Sci.*, 3: 1505-1518 (2015).
Korean Intellectual Property Office, International Search Report and Written Opinion in International Application No. PCT/US2017/044234, dated Nov. 8, 2017.
Hadrami et al., "Chitosan in Plant Protection," *Mar. Drugs*, 8(4): 968-987 (2010).
Rabea et al., "Chitosan as Antimicrobial Agent: Applications and Mode of Action," *Biomacromolecules*, 4(6): 1457-1465 (2003).
"Aquazol: The Basics," Polymer Chemistry (2013) [obtained at https://www.polychemistry.com/aquazol].
Dhanalakshmi et al., "Photocatalytic and antimicrobial activities of functionalized silicate sol-gel embedded ZnO—TiO2 nanocomposite materials," *Mater. Express*, 3(4): 291-300 (2013).
Gao et al., "Studies on the preparation and antibacterial properties of quaternized polyethyleneimine," *J. Biomater. Sci. Polym. Ed.*, 18(5): 531-544 (2007).
Livingstone, "PEI Transfection Patents to Expire," Tebu-Bio Blog (Jul. 7, 2015) [obtained at https://tebu-bio.com/blog/2015/07/02/pei-transfection-patents-to-expire].
Pasquier et al., "From Multifunctionalized Poly(ethylene imine)s toward Antimicrobial Coatings," *Biomacromolecules*, 8(9): 2874-2882 (2007).
Rizzo et al., "Effect of solar simulated N-doped TiO2 photocatalysis on the inactivation and antibiotic resistance of an *E. coli* strain in biologically treated urban wastewater," *Applied Catalysis B: Environmental*, 144: 369-378 (2014).
Rozenberg et al., "Polymer-assisted fabrication of nanoparticles and nanocomposites," *Prog. Polym. Sci*, 33(1): 40-112 (2008).
Salwiczek et al., "Emerging rules for effective antimicrobial coatings," *Trends Biotechnol.*, 32(2): 82-90 (2014).
Shenglu Kuang, "Modern Fine Chemical Technology and Product Synthesis Process", Scientific and Technical Documentation Press (Sep. 1997).
China National Intellectual Property Administration, Office Action and Search Report in Chinese Patent Application No. 201780052448.X (dated Sep. 4, 2020).
China National Intellectual Property Administration, Second Office Action in Chinese Patent Application No. 201780052448.X (dated Mar. 16, 2021).
Japanese Patent Office, Notice of Reasons for Refusal in Japanese Patent Application No. 2019-526199 (dated Sep. 29, 2020).
Clarke et al., "The Action of Formaldehyde on Amines and Amino Acids," *JACS*, 55(11): 4571-4587 (1933).
Thind et al., "Significant enhancement in the photocatalytic activity of N, W co-doped $TiO_2$ nanomaterials for promising environmental applications," *Nanotechnology*, 23(47): 475706 (2012).

* cited by examiner

POLYMER-BASED ANTIMICROBIAL COMPOSITIONS AND METHODS OF USE THEREOF

CROSS-REFERENCE TO RELATED APPLICATIONS

This patent application is a divisional of U.S. patent application Ser. No. 15/662,119, filed Jul. 27, 2017, which claims the benefit of U.S. Provisional Patent Application No. 62/488,421, filed Apr. 21, 2017, and U.S. Provisional Patent Application No. 62/368,008, filed Jul. 28, 2016, each of which is incorporated by reference.

BACKGROUND OF THE INVENTION

Infectious diseases kill more people worldwide each year than any other single cause. Minimizing infections caused by pathogenic microorganisms is a great concern in many fields, particularly in medical devices, drugs, hospital surfaces/furniture, dental restoration and surgery equipment, healthcare products and hygienic applications, water purification systems, textiles, food packaging and storage, industrial or domestic appliances, aeronautics, etc. Particularly in hospitals, great efforts and significant costs are incurred in the fight against infections.

Infections are produced by touching, eating, drinking, or breathing something that contains a pathogen. It is estimated that 80% of human infections occur as a result of contact with microbe-contaminated surfaces (Salwiczek et al., *Trends Biotechnol* 32: 82-90 (2014)). Generally, these infections are combated with antimicrobial agents that target the pathogen. Particularly problematic, however, are the microorganisms that can rapidly and easily mutate their genes to become resistant to these agents, making their elimination difficult. For instance, *Staphylococcus aureus* (*S. aureus*) commonly colonizes human skin and mucosa without causing severe problems, but if the bacteria enter the body, illnesses that range from mild to life-threatening can develop, including skin and wound infections, infected eczema, abscess infections, heart valve infections or endocarditis, pneumonia, and bloodstream infections or bacteraemia. Some *S. aureus* are resistant to methicillin and other β-lactam antibiotics—methicillin-resistant *S. aureus* (MRSA)—and require alternative types of antibiotics to treat them. Moreover, the spore-forming *Clostridium difficile* (*C. difficile*), an intestinal superbug causing symptoms ranging from diarrhea to life-threatening inflammation of the colon, is the most common bacterial infection acquired in hospitals.

Over the past several years, there have been a growing number of researchers working on new antimicrobial systems aimed at helping to mitigate, combat and/or eradicate costly debilitating infections. Much of this research has focused on polymers due to their intrinsic properties: polymers can act as a matrix for holding antimicrobial agents and their characteristics, such as their hydrophilicity and/or molecular weight, can have a great influence on the resulting antimicrobial activity. Therefore, the use of polymeric materials with antimicrobial properties has attracted increasing interest from both the academic and industrial community.

Known antimicrobial polymer coatings have been prepared by impregnating, adsorbing, or covalently attaching antimicrobial agents to various surfaces in order to provide a filmed layer. For example: U.S. Pat. No. 9,127,173 discloses preparing a layer by layer coating on a substrate, in which the coating comprises quaternary amine groups that impart antibacterial properties to the substrate. Non-leaching surfaces are often considered preferable because microbes are exposed to high surface concentrations of the antimicrobial agent compared with slow-release surfaces. Moreover, leaching surfaces make it difficult to pass the Environmental Protection Agency (EPA) cytotoxicity tests. As a general rule, non-leaching antimicrobial coatings and preparation methodologies are extremely complex and impractical for large-scale production and commercialization. Furthermore, this technique is generally surface specific. Alternative approaches to the preparation of antimicrobial coatings include the use of coatings that are non-covalently linked to the surface. However, similar to the covalently linked coatings, these methodologies generally require complex multiple synthetic steps and need to be adjusted for coating different substrates, thus making them impractical for commercial use.

Therefore, despite active research in this area, there remains a need for novel antimicrobial materials that exhibit broad-spectrum antimicrobial activity and that can easily be adapted to the complexity of different environments (e.g., homes, healthcare providers, schools, agriculture), surfaces (e.g., wood, stainless steel, marble, glass, and textiles), and applications (e.g., food packaging, water or air filters, or even protecting fruits and vegetables). In addition, such an antimicrobial residual self-sanitizing film or coating should ideally provide a very high kill rate, be viable for weeks, be non-toxic yet easily removed. It would also be desirable to have a versatile and inexpensive process for preparing such surface coatings on a commercial scale.

BRIEF SUMMARY OF THE INVENTION

The invention is predicated on a polymer-based antimicrobial composition that is non-toxic, water soluble, and that significantly mitigates the transmission of infectious diseases from surfaces, such as glass, plastic, granite, and metallic substrates as well as skin. The polymers used in the compositions are capable of serving two functions: (i) the ability to disinfect surfaces by killing existing germs (kill-now); and (ii) providing a removable, residual self-sanitizing film that prevents future microbial growth (kill-later). The polymer-based composition is effective against bacteria, viruses, and spores, including *Clostridium difficile* (*C. difficile*). Additionally, unlike most commercial disinfectants the polymer-based composition inactivates non-enveloped viruses, which typically are the cause of the common cold and gastro-intestinal flu. Because the antimicrobial composition does not require germicidal chemicals or metals, the composition is safe for humans, animals, and the environment, unlike many other commercial disinfectants.

The invention provides a polymer-based antimicrobial composition comprising a cationic polymer, at least one adhesion promoter, a carrier, and optionally organic and/or inorganic particles that are photocatalytically active in visible light, wherein the components of the composition are not covalently bound to one another. The antimicrobial composition is in accordance with at least one of the following tests:

(i) a germicidal spray test according to American Society for Testing and Materials (ASTM) international method E1153 that meets the EPA requirement of log 3 reduction for viruses and a log 5 reduction for bacteria, (ii) a suspension test according to ASTM international method E1052-96 (2002) or ASTM international method E2315 (2016), (iii) a film formed from the composition kills
  (iii-a) at least 95% of log 5 population of a gram positive or gram negative bacteria in 30 minutes,
  (iii-b) at least 95% of log 4 population of an enveloped virus within 30 minutes of contact of contact,
  (iii-c) at least 95% of a non-enveloped virus within 30 minutes of contact, and/or
  (iii-d) at least 94% of a log 4 population of *Clostridium difficile* bacteria within 24 hours of contact, in accordance with Japanese Industrial Standard (JIS) Z 2801 (2006) test for antimicrobial activity, or a modified version of such test as described herein,
(iv) a film formed from the composition has a value of 2 or less according to International Organization for Standardization (ISO) 10993-5 in vitro cytotoxicity test,
(v) a durability test selected from either (v-a) a film formed from the composition kills at least 99.9% of gram-positive bacteria and gram-negative bacteria according to EPA Protocol #01-1A residual self-sanitizing activity test, or (v-b) waiting 7 days after film formation, a film formed from the composition kills at least 95% of gram-positive bacteria and gram-negative bacteria, or enveloped and non-enveloped viruses according a modified version of Protocol #01-1A residual self-sanitizing activity test, as described herein.

The invention also provides a method of killing microbes on a surface comprising applying to the surface the antimicrobial composition comprising a cationic polymer, at least one adhesion promoter, a carrier, and optionally organic and/or inorganic particles that are photocatalyically active in visible light.

The invention further provides a method of killing microbes on a surface comprising applying to the surface an antimicrobial composition comprising a high molecular weight polydiallyldimethylammonium salt and a carrier.

The invention further provides a composition comprising a polyethylenimine-based polymer, optionally a second cationic polymer selected from a polydiallyldialkylammonium salt, a poly(acrylamide-co-diallyldialkylammonium halide), chitosan, or a combination thereof, optionally a polyacid, and a carrier. Also provided is an antimicrobial composition comprising at least one organic and/or inorganic particle that is photocatalytically active in visible light, at least one adhesion promoter, and a carrier. These compositions can be used in a method of killing microbes on a surface.

DETAILED DESCRIPTION OF THE INVENTION

Figure 1:
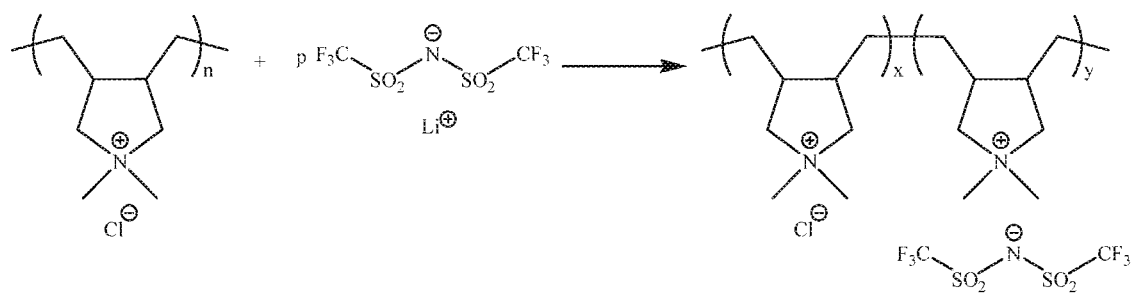
FIG. 1 illustrates counter-ion exchange in the polydiallyldimethylammonium chloride (polyDADMAC) by LiTFSI in an embodiment of the invention.

The invention provides a polymer-based antimicrobial composition comprising a cationic polymer, at least one adhesion promoter, optionally organic and/or inorganic particles that are photocatalytically active in visible light, and a carrier, wherein the components of the composition are not covalently bound to one another. The antimicrobial composition is in accordance with at least one of the following tests:
  (i) a germicidal spray test according to ASTM E1153 that meets the EPA requirement of log 3 reduction for viruses and a log 5 reduction for bacteria,
  (ii) a suspension test according to ASTM E1052-96 (2002) or ASTM E2315 (2016),
  (iii) a film formed from the composition kills
    (iii-a) at least 95% of log 5 population of a gram positive or gram negative bacteria in 30 minutes,
    (iii-b) at least 95% of log 4 population of an enveloped virus within 30 minutes of contact of contact,
    (iii-c) at least 95% of a non-enveloped virus within 30 minutes of contact, and/or
    (iii-d) at least 94% of a log 4 population of *Clostridium difficile* bacteria within 24 hours of contact,
in accordance with JIS Z 2801 (2006) test for antimicrobial activity, or a modified version of such test as described herein,
  (iv) a film formed from the composition has a value of 2 or less according to International Organization for Standardization (ISO) 10993-5 in vitro cytotoxicity test,
  (v) a durability test selected from either (v-a) a film formed from the composition kills at least 99.9% of gram-positive bacteria and gram-negative bacteria according to EPA Protocol #01-1A residual self-sanitizing activity test, or (v-b) waiting 7 days after film formation, a film formed from the composition kills at least 95% of gram-positive bacteria and gram-negative bacteria, or enveloped and non-enveloped viruses according a modified version of Protocol #01-1A residual self-sanitizing activity test, as described herein.

The effectiveness of the antimicrobial composition, described herein, is best viewed in terms of the following advantages. The composition has the ability to "kill now" when applied to a surface as a traditional disinfectant—even without the presence of conventional germicidal chemicals that can be toxic. The composition has the ability to "kill later," i.e., to kill persistently (sanitize) into the future post-application by forming a residual self-sanitizing film that passes an EPA-acceptable durability test and EPA-approved toxicity tests, as described herein. The residual self-sanitizing film is removable with water (e.g., warm soapy water), alcohol, or a water-alcohol mixture. The technology is highly tunable because: i) the composition can be tuned to create films of various thicknesses, solvency, and adhesion, ii) one or more cationic polymers can be mixed in particular proportions so as to target specific pathogens and/or to design products with various cost profiles, and/or iii) the natural "kill-now" feature stemming from the cationic polymer can be augmented, if desired, by adding one or more conventional antimicrobial agents to the composition. These and other advantages of the invention, as well as additional inventive features, will be apparent from the description of the invention provided herein.

The antimicrobial composition comprises at least one cationic polymer. The cationic polymer can be any suitable cationic polymer of a molecular weight and charge density that demonstrates an antimicrobial property and enables the composition or a film formed from the composition to pass at least one of tests (i)-(v). It was determined that charge density is influenced by the molecular weight and pH of the formulation. For example, charge tends to be increased with higher molecular weight. Alternatively, or in addition, charge tends to be increased with lower pH. Thus, the molecular weight and/or the pH can be modified to provide a desired charge density and/or antimicrobial activity. Suitable molecular weights of various cationic polymers are described herein. The pH of the composition typically is less than about 7, such as a pH between about 3-7, more preferably a pH between about 4-6.

Without wishing to be bound to any particular theory, the cationic polymer is highly effective at, inter alia, targeting gram-positive and/or gram-negative bacteria and enveloped and non-enveloped viruses. In particular, it is believed that the positively charged polymer attracts and binds to a microbe particle, such as a virus particle. The polymer continues to encapsulate the microbe. Once the polymer fully encapsulates the microbe, the capsid is destroyed, which results in a harmless release of the genomic material.

Specific examples of a suitable cationic polymer include a polydiallyldialkylammonium salt, an acryloxyalkyltrialkylammonium salt (e.g., acryloxyethyltrimethylammonium halide, methacryloxyethyltrimethylammonium halide), a vinylphenalkyltrialkylammonium salt (e.g., vinylbenzyltrimethylammonium halide), an acrylamidoalkyltrialkylammonium salt (e.g., 3-acrylamido-3-methylbutyltrimethylammonium halide), a poly(acrylamide-co-diallyldialkylammonium salt) (e.g., poly(acrylamide-co-diallyldimethylammonium chloride)), a polyethylenimine-based polymer, chitosan, or a combination thereof. In any of the foregoing polymers, each alkyl group is the same or different and is a straight chain $C_{1-6}$ or branched $C_{3-6}$ (e.g., methyl, ethyl, t-butyl) group, and the salt is an anion, such as a halide (e.g., chloride, fluoride, bromide), a halide-containing anion (e.g., bis(triflouromethane)sulfonimide, trifluoroacetate), a sulfate, or a phosphate. Preferably, the cationic polymer is a polydiallyldialkylammonium salt (e.g., polydiallyldimethylammonium halide), a poly(acrylamide-co-diallyldialkylammonium halide) (e.g., poly(acrylamide-co-diallyldimethylammonium chloride)), and/or a polyethylenimine-based polymer (e.g., linear, non-chemically modified PEI). In some embodiments, the composition does not contain a bridged polycyclic compound (e.g., a cavitand structure), including a polymer-bound bridged polycyclic compound (e.g., a polymer-bound cavitand). In some embodiments, the cationic polymer is not a hybrid material that comprises one or more divalent metals and siloxane bridges.

In some instances, a combination of two or more cationic polymers selected from a polydiallyldialkylammonium salt (e.g., polydiallyldimethylammonium halide), an acryloxyalkyltrialkylammonium salt, a vinylphenalkyltrialkylammonium salt, an acrylamidoalkyltrialkylammonium salt, a poly(acrylamide-co-diallyldialkylammonium halide), a polyethylenimine-based polymer, and chitosan are used in the composition. In a particular embodiment, a polydiallyldialkylammonium salt (e.g., polydiallyldimethylammonium halide) is used in combination with a polyethylenimine-based polymer (e.g., a linear or branched polyethylenimine (PEI)). In a preferred embodiment, polydiallyldimethylammonium chloride or poly(acrylamide-co-diallyldialkylammonium chloride) is used in combination with a non-chemically modified linear PEI.

The cationic polymer may or may not be used in concert with an anionic polymer to form a polyelectrolyte complex (PEC). As used herein, PEC refers to the complex that forms automatically upon addition of one or more cationic polymers in concert with one or more anionic polymers. A PEC typically is hydrophilic and tends to be water soluble. In some embodiments, the composition does not comprise an anionic polymer. When the cationic polymer is a polydiallyldialkylammonium salt (e.g., a polydiallyldialkylammonium halide), the formation of a PEC is optional, i.e., an anionic polymer is optional in the composition. In some embodiments, the composition does not comprise an anionic polymer in combination with a polydiallyldialkylammonium salt (e.g., a polydiallydimethylammonium halide).

In an embodiment, the cationic polymer is a polydiallyldialkylammonium salt, such as a polydiallyldialkylammonium halide (e.g., a halide or halide-containing anion), a polydiallyldialkylammonium sulfate, or polydiallyldialkylammonium phosphate. In the polydiallyldialkylammonium halide, the halide can be any suitable compound in which the anion is a halide or includes a halide (e.g., bis(triflouromethane)sulfonimide, trifluoroacetate), such as, polydiallyldimethylammonium fluoride, polydiallyldimethylammonium chloride, polydiallyldimethylammonium bromide, polydiallyldimethylammonium iodide, polydiallyldimethylammonium bis(triflouromethane)sulfonimide or a combination thereof. In preferred embodiments, the polydiallyldimethylammonium halide is polydiallyldimethylammonium fluoride, polydiallyldimethylammonium chloride (polyDADMAC), or a mixture of polydiallyldimethylammonium chloride and polydiallyldimethylammonium fluoride and/or polydiallyldimethylammonium bis(triflouromethane)sulfonimide.

Preferred polydiallyldialkylammonium salts are those polymers made from polymerization of diallyldialkylammonium compounds, which can be represented by the following formula:

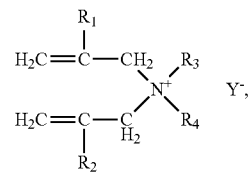

in which $R_1$ and $R_2$ are the same or different and each is hydrogen or $C_1$-$C_6$ alkyl; $R_3$ and $R_4$ are, independently, hydrogen or an alkyl, hydroxyalkyl, carboxyalkyl, carboxyamidalkyl or alkoxyalkyl group with 1 to 12 carbon atoms; and $Y^-$ represents an anion such as a halide, a halide-containing anion (e.g., bis(triflouromethane)sulfonimide), a sulfate, or a phosphate. Examples of the preferred diallyldialkylammonium monomer include diallyldimethylammonium chloride (DADMAC), diallyldimethylammonium fluoride, diallyldimethylammonium bis(triflouromethane)sulfonimide, diallyldimethylammonium bromide, diallyldimethylammonium sulfate, diallyldimethylammonium phosphate, dimethyallyldimethylammonium chloride, dimethyallyldimethylammonium fluoride, dimethyallyldimethylammonium bis(triflouromethane)sulfonimide, diethylallyldimethylammonium chloride, diethylallyldimethylammonium fluoride, diethylallyldimethylammonium bis(triflouromethane)sulfonimide, diallyldi(beta-hydroxyethyl)ammonium chloride, diallyldi(beta-hydroxyethyl)ammonium fluoride, diallyldi(beta-hydroxyethyl)ammonium bis(triflouromethane)sulfonimide, diallyldi(beta-ethoxyethyl)ammonium chloride, diallyldi(beta-ethoxyethyl)ammonium fluoride, diallyldi(beta-ethoxyethyl)ammonium bis(triflouromethane)sulfonimide, diallyldiethylammonium chloride, diallyldiethylammonium fluoride, and diallyldiethylammonium bis(triflouromethane)sulfonimide. In a preferred embodiment, the cationic polymer is polyDADMAC.

In a particular embodiment, some of the polyDADMAC molecular chloride counterions can be converted into insoluble fluoride-containing counterions. Such conversion can occur, for example, by adding a dilute mixture of lithium bis(triflouromethane)sulfonimide (LiTFSI). LiTFSI, as well as polyDADMAC, bears electrostatic charges that endows the moiety with a (poly)electrolyte behavior in solution. This counter-ion exchange in the polyDADMAC by LiTFSI is illustrated in FIG. 1. LiTFSI is known to have a good solubility and stability in water. The reaction of exchange consists of mixing two solutions: one containing the positively charged polyDADMAC and the other containing the negatively charged TFSI⁻ anions. When a sufficient fraction of the polymer counter-anions has been exchanged for TFSI⁻ anions, the polymer becomes insoluble, and precipitates from the solution. TFSI⁻ anions in the solution either can be linked to a polymer chain or can be part of a micelle. The present invention seeks to use the ion-exchange strategy to create only enough micelles to slightly decrease the solubility of the cationic polymer whether used by itself or in a PEC film. The addition of the TFSI⁻ anions decrease the polymer's solubility but increases the resulting film's durability relative to the EPA Protocol #01-1A residual self-sanitizing activity test, or a modification thereof, as described herein. Desired solubility is achieved by experimentally determining the amount of TFSI⁻ that will yield the desired reduction in solubility. In a specific example, the following steps can be used: 1) initially reduce the water added to the polyDADMAC solution by 125 ml; 2) create a dilute solution of TFSI by mixing into the solution 0.125 to 0.250 grams of TFSI for every 2.4 gram of polyDADMAC; then 3) drizzle this dilute solution into the polyDADMAC solution. The method is carried out at room temperature with vigorous stirring for 24 hours, which is necessary to ensure a homogeneous distribution. This mixture can, if desired, be used to create a PEC with one or more anionic polymers. If a PEC is desired in such an embodiment, the partial replacement of the counter ions in the water-soluble polyDADMAC is achieved by adding a dilute solution of TFSI⁻ before introducing an anionic polymer to create the PEC.

The counter-ion transformation strategy of polyDADMAC does not adversely affect its antimicrobial activity. To test the activity, excess TFSI⁻ was used to create a precipitate that was then dissolved in dimethyl sulfoxide (DMSO). This solution was then placed on a slide to create a film that was held for 7 days and then inoculated with a log 6 population of *Escherichia coli* (*E. coli*). The transformed polyDADMAC with a mix of fluoride and chloride ions provided a film that was able to kill >99.99% of the *E. coli* population within 30 minutes.

The polydiallyldialkylammonium salt (e.g., polydiallyldimethylammonium halide), acryloxyalkyltrialkylammonium salt, vinylphenalkyltrialkylammonium salt, and/or acrylamidoalkyltrialkylammonium salt preferably has a number average molecular weight between 25,000 g/mol and 20,000,000 g/mol. A higher molecular weight typically is preferred in order to reduce the solubility of a film formed from the antimicrobial composition. The polydiallyldialkylammonium salt (e.g., polydiallyldimethylammonium halide), acryloxyalkyltrialkylammonium salt, vinylphenalkyltrialkylammonium salt, and/or acrylamidoalkyltrialkylammonium salt can have a number average molecular weight of 20,000,000 g/mol or less, for example, 15,000,000 g/mol or less, 10,000,000 g/mol or less, 5,000,000 g/mol or less, or 1,000,000 g/mol or less. Alternatively, or in addition, the polydiallyldialkylammonium salt, acryloxyalkyltrialkylammonium salt, vinylphenalkyltrialkylammonium salt, and/or acrylamidoalkyltrialkylammonium salt can have a number average molecular weight of 25,000 g/mol or more, for example, 50,000 g/mol or more, 100,000 g/mol or more, 150,000 g/mol or more, 200,000 g/mol or more, 250,000 g/mol or more, 300,000 g/mol or more, 350,000 g/mol or more, 400,000 g/mol or more, 450,000 g/mol or more, 500,000 g/mol or more, 550,000 g/mol or more, 600,000 g/mol or more, 650,000 g/mol or more, 700,000 g/mol or more, 750,000 g/mol or more, or 800,000 g/mol or more. Thus, the polydiallyldialkylammonium salt, acryloxyalkyltrialkylammonium salt, vinylphenalkyltrialkylammonium salt, and/or acrylamidoalkyltrialkylammonium salt can have a number average molecular weight bounded by any two of the aforementioned endpoints. For example, the polydiallyldialkylammonium salt, acryloxyalkyltrialkylammonium salt, vinylphenalkyltrialkylammonium salt, and/or acrylamidoalkyltrialkylammonium salt can have a number average molecular weight between 25,000 g/mol and 20,000,000 g/mol, between 25,000 g/mol and 15,000,000 g/mol, between 25,000 g/mol and 10,000,000 g/mol, between 25,000 g/mol and 5,000,000 g/mol, between 25,000 g/mol and 1,000,000 g/mol, between 50,000 g/mol and 1,000,000 g/mol, between 100,000 g/mol and 1,000,000 g/mol, between 150,000 g/mol and 1,000,000 g/mol, between 200,000 g/mol and 1,000,000 g/mol, between 250,000 g/mol and 1,000,000 g/mol, between 300,000 g/mol and 1,000,000 g/mol, between 350,000 g/mol and 1,000,000 g/mol, or between 400,000 g/mol and 1,000,000 g/mol. In some embodiments, polydiallyldialkylammonium salt, acryloxyalkyltrialkylammonium salt, vinylphenalkyltrialkylammonium salt, and/or acrylamidoalkyltrialkylammonium salt has a number average molecular weight between 250,000 g/mol and 1,000,000 g/mol or between 800,000 g/mol and 1,000,000 g/mol, including between 900,000 g/mol and 1,000,000 g/mol.

In some embodiments, the polydiallyldialkylammonium salt is "an ultra-high molecular weight" polydiallyldialkylammonium salt, such as an ultra high molecular weight polydiallyldimethylammonium halide. The ultra-high molecular weight polydiallyldialkylammonium salt (e.g., polydiallyldimethylammonium halide) typically has a number average molecular weight between about 800,000 g/mol and about 20,000,000 g/mol (e.g., between about 1,000,000 g/mol and 15,000,000 g/mol, between about 1,000,000 g/mol and 10,000,000 g/mol, between about 1,000,000 g/mol and 5,000,000 g/mol, between about 2,000,000 g/mol and 5,000,000 g/mol, between about 3,000,000 g/mol and 5,000,000 g/mol, between about 4,000,000 g/mol and 10,000,000 g/mol, between about 5,000,000 g/mol and 20,000,000 g/mol, between about 5,000,000 g/mol and 15,000,000 g/mol, between about 6,000,000 g/mol and 20,000,000 g/mol, and between about 6,000,000 g/mol and 15,000,000 g/mol). In these embodiments, generally, the halide in polydiallyldialkylammonium halide is fluoride, chloride, including anions containing fluoride and/or chloride. In particular, the polydiallyldialkylammonium halide is polyDADMAC or a mixture of polyDADMAC and polydiallyldimethylammonium fluoride and/or polydiallyldimethylammonium bis(triflouromethane)sulfonimide.

In another embodiment, the cationic polymer is a polyethylenimine-based polymer, which typically is effective against non-enveloped viruses, which account for a large number of pathogenic microbes, such as rhinovirus, poliovirus, adenoviruses, coxsackievirus, parvovirus, and rotavirus. The polyethylenimine-based polymer can be any suitable polyethylenimine-based polymer that is linear or non-linear, preferably linear.

There are a number of reports of polyethylenimine (PEI) that has been chemically modified to create an antimicrobial agent. See, for example, Gao et al. (*J. Biomaterial Science, Polymer Edition*, 2007, 18, 531-544) reported that quaternized branched PEI (BPEI) was antimicrobial against *Escherichia coli* (*E. coli*) at low concentrations. Pasquier et al. (*Biomacromolecules*, 2007, 8, 2874-2882) reported that BPEI quaternized with various long alkyl groups exhibited some degree of antimicrobial activity against *E. coli*, while linear PEI (LPEI) grafted with long alkyl chains produced a series of hydrophobically-modified water insoluble LPEI derivatives that effectively killed *E. coli* and *Staphyloccocus aureus*. See also, U.S. Pat. No. 9,399,044 and WO 2008/127416 A2. For example, the chemically modified PEI described in U.S. Pat. No. 9,399,044 is only effective against bacterium (e.g., Tuberculosis *mycobacterium*, gram negative *E. coli* and *Pseudomonas aeruginosa*, gram positive *Staphylococcus aureus*) and the fungus *Candida albicans*, but not viruses. WO 2008/127416 A2 demonstrates that an antimicrobial coating comprising a chemically modified PEI is capable of killing enveloped viruses but not non-enveloped viruses, as shown in Table 1.

TABLE 1

| Strain | Initial Viral Titer (pfu/ml) | Final Viral Titer (pfu/ml) Uncoated slide | Final Viral Titer (pfu/ml) Coated slide | Virus Titer Reduction |
|---|---|---|---|---|
| A/Wuhan/359/95 | (4.8 ± 0.5) × 10$^5$ | (3.1 ± 0.4) × 10$^3$ | 0 | 100% (>3.5 logs) |
| A/turkey/MN/833/80 | (6.1 ± 1.1) × 10$^6$ | (3.7 ± 0.4) × 10$^4$ | 0 | 100% (>4.5 logs) |

However, chemical modification requires expensive, low yield, organic chemical processes that use toxic chemicals that are harmful to humans and the environment. Thus, in some embodiments of the invention, the polyethylenimine-based polymer is linear PEI that has not been chemically or structurally modified (e.g., does not include alkyl and/or quaternary ammonium groups). Moreover, it was discovered that non-chemically modified linear PEI can kill non-enveloped viruses. In particular, a film of the non-chemically modified linear PEI described herein kills not only gram positive and gram negative bacteria but also demonstrates at least a log 4 (99.99%) reduction against both enveloped and non-enveloped viruses, which is particularly important because many non-enveloped viruses are the pathogenic microbes that cause common colds and gastrointestinal flu, such as rhinovirus, poliovirus, adenoviruses, coxsackievirus, parvovirus, and rotavirus. The ability of an antimicrobial composition comprising non-chemically modified, linear PEI to reduce an MS2 bacteriophage, which is considered to be a surrogate for a non-enveloped virus, is demonstrated in Table 2.

TABLE 2

| Micro-organism | Contact Time | Test Substance | PFU/Carrier | Percent Reduction Compared to Parallel Control | Log$_{10}$ Reduction Compared to Parallel Control |
|---|---|---|---|---|---|
| MS2 bacteriophage ATCC | Initial 5 min | Inoculum Parallel control | 4.00E+05 1.60E+05 | n/a | |

TABLE 2-continued

| Micro-organism | Contact Time | Test Substance | PFU/Carrier | Percent Reduction Compared to Parallel Control | Log$_{10}$ Reduction Compared to Parallel Control |
|---|---|---|---|---|---|
| | | 15597-B1 Non-chemically modified, linear PEI, 6K ppm, pH 6.4 | 1.00E+01 | 99.994% | 4.20 |

In other embodiments, the polyethylenimine-based polymer is a deacylated PEI or a quaternized N-alkyl-N-methylpolyethylenimine. The deacylated polyethylenimine can be supplied by a commercial source, such as Polysciences, Inc. (Warrington, Pa.). As used herein, "deacylated polyethylenimine" refers to a polyethylenimine with protonatable nitrogens and of the formula:

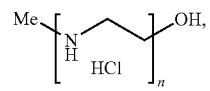

wherein the polymer has been partially (at least 10%, at least 20%, at least 30%, at least 40%, at least 50%, at least 60%, at least 70%, at least 80%, or at least 90%) or fully (about 98-100%) hydrolyzed (deacylated). Without wishing to be bound to any particular theory, it is believed that dealkylation strengthens PEI's ability to kill viruses and decreases its cytotoxicity.

As used herein, "quaternized-N-alkyl-N-methylpolyethylenimine" refers to a polyethylenimine that has been partially (at least 10%, at least 20%, at least 30%, at least 40%, at least 50%, at least 60%, at least 70%, at least 80%, or at least 90%) or fully (about 98-100%) hydrolyzed, methylated, then quaternized with an alkyl substituent. The alkyl substituent in this embodiment can be any suitable alkyl substituent that is straight chain or branched. Generally, the alkyl substituent has a chain length chosen to be most effective against viruses, e.g., $C_{1-18}$, including $C_{8-14}$ and $C_{10-12}$. In an embodiment, the alkyl substituent is decane, dodecane, or hexadecane.

A synthetic route to providing a PEI that is fully hydrolyzed (deacylated), methylated, and then quaternized includes the following method steps:

Step 1: Prepare a fully deacetylated linear PEI by the acid-catalyzed hydrolysis of commercial PEOZs (e.g., 500 kDa, 200 kDa, and 50 kDa, preferably 50 kDa). For example, 10.0 g of the PEOZs was added to 400 mL of 24% (wt/vol) HCl, followed by refluxing for 96 h. The POEZ crystals dissolved completely in 2h, but 3h later, (i.e., total of 5h) a white precipitate appeared. The precipitate in each case was isolated by filtration and then air-dried.

The protonated PEOZ (2-ethyl-2-oxazoline) was then deprotonated using an aqueous base (e.g., KOH) solution. Briefly, 10 g of protonated linear PEI was dissolved in distilled water (50 mL), and 6 M KOH was added until the pH of the solution became ~11. The fully deprotonated PEIs appeared as a white precipitate, which was filtered and washed repeatedly with distilled water until it became neutral (pH ~7). The end product was a linear PEI without N-acyl groups having a molecular weight of approximately 217 kDa, 87 kDa, or preferably 22 kDa.

Step 2: The E. Clarke methylation technique (Clarke et al., JAGS, 55(11): 4571 (1933)) can be used to create linear N-Methyl-PEI. A 50% aqueous solution of PEI consisting of 10 g of 22 kDa PEI created in step 1 was transferred to a round-bottom flask to which 90% formic acid (24.5 mL, 0.48 mol) was added followed by 37% formaldehyde (29.3 mL, 0.36 mol) and 20 mL of water. The reaction mixture was stirred at 90° C. for 96h. After cooling to room temperature, the pH of the reaction mixture was adjusted to 11 using an 8M KOH solution. The deprotonated N-methylated PEI was extracted several times with chloroform, and the entire organic solution was subjected to repeated water wash. Chloroform was then removed to yield a yellow viscous N-methylated PEI with 100% degree of methylation.

Step 3: N-Alkyl N-Methyl PEI was then quaternized to be water soluble and target viruses. In particular, 1g (17.5 mmol/repeating unit) of N-methylated PEI was dissolved in 75 ml tert-butanol in a screw-top pressure tube. To this was added 1-bromohexadecane, to provide the side chain lengths that are most effective against viruses. The reaction mixture then was heated at 105° C. for 48h to 96h, depending upon the desired solubility of the end product. After completing the reaction, the solvent was removed to one-tenth of its initial volume. Then, an excess of acetone (200 mL) was added to the reaction mixture, and the precipitate was filtered off. To further purify the product, the precipitate was dissolved in chloroform, and acetone was added to re-precipitate the product. The excess solvent was decanted off, and the precipitate was dried using a high vacuum pump to yield a linear N-alkyl N-methyl PEI polymer.

The polyethylenimine-based polymer typically has a number average molecular weight between 15,000 g/mol and 250,000 g/mol. The polyethylenimine-based polymer can have a number average molecular weight of 250,000 g/mol or less, for example, 230,000 g/mol or less, 210,000 g/mol or less, 190,000 g/mol or less, or 170,000 g/mol or less. Alternatively, or in addition, the polyethylenimine-based polymer can have a number average molecular weight of 15,000 g/mol or more, for example, 30,000 g/mol or more, 60,000 g/mol or more, 90,000 g/mol or more, 100,000 g/mol or more, 120,000 g/mol or more, or 150,000 g/mol or more. Thus, the polyethylenimine-based polymer can have a number average molecular weight bounded by any two of the aforementioned endpoints. For example, the polyethylenimine-based polymer can have a number average molecular weight between 15,000 g/mol and 250,000 g/mol, between 15,000 g/mol and 230,000 g/mol, between 15,000 g/mol and 210,000 g/mol, between 15,000 g/mol and 190,000 g/mol, between 15,000 g/mol and 170,000 g/mol, between 30,000 g/mol and 170,000 g/mol, between 60,000 g/mol and 170,000 g/mol, between 90,000 g/mol and 170,000 g/mol, between 120,000 g/mol and 170,000 g/mol, or between 150,000 g/mol and 170,000 g/mol, e.g., about 160,000 g/mol.

An aspect of the invention is an antimicrobial composition comprising (a) a polydiallyldialkylammonium salt (e.g., polydiallyldimethylammonium halide) is used in combination with a polyethylenimine-based polymer (e.g., a linear or branched polyethylenimine (PEI), preferably linear PEI), (b) at least one adhesion promoter, (c) optionally organic and/or inorganic particles that are photocatalytically active in visible light, (d) optionally at least one salt, and (e) a carrier, each of which is described herein. The antimicrobial composition passes at least one of tests (i)-(v). The weight ratio of polydiallyldialkylammonium salt to polyethylenimine-based polymer is any suitable amount, but typically ranges from 80/20 to 20/80 (e.g., 30/70, 33/67, 40/60, 45/55, 50/50, 55/45, 60/40, 67/33, 70/30). In a particular example, the weight ratio of polyDADMAC:PEI is 50/50 or 33/67.

When the cationic polymer is a polyethylenimine-based polymer, the composition can further comprise an anionic polymer, such that the cationic polymer and anionic polymer combine to form a PEC. In some embodiments, the polyethylenimine-based polymer, such as non-chemically modified linear PEI, is used without an anionic polymer, such as a polyacrylic acid salt. In other embodiments in which a PEC is desired, the composition comprises both a polydiallyldialkylammonium salt (e.g., polydiallyldimethylammonium halide) and PEI, such as a branched PEI. Two approaches are suggested for adding PEI to the system. One approach is to first complex the polydiallyldialkylammonium halide and anionic polymer and then complex the PEI to the anionic polymer, followed by the blending of the two complexes. The second, and preferred, approach is to simultaneously complex both cationic polymers with the anionic polymer in a one-pot synthesis.

It is known by those skilled in the art that non-enveloped viruses are resistant to ethanol, which is the alcohol most commonly used in hand sanitizers and other disinfectants. The inventors discovered that a composition of ethanol and non-chemically modified linear PEI is effective at killing non-enveloped viruses and that the antimicrobial activity can be further improved by adding an organic small molecule polyacid, such as citric acid. Without wishing to be bound by any theory, it is believed that protonated liner PEI binds the anionic form of the polyacid (e.g., citrate) to form a complex. Suitable organic polyacids include a polycarboxylic acid comprising at least three carboxylic acid groups (e.g., 3, 4, 5, and/or 6 carboxylic acid groups), such as an organic tribasic acid. Specific examples of a polycarboxylic acid include citric acid, isocitric acid, aconitic acid, propane-1,2,3-tricarboxylic acid, hemimelitic acid, trimellitic acid, trimesic acid, prehnitic acid, meallanophanic acid, pyromellitic aicd, benzenepentacarboxylic acid, mellitic acid, ethylenediamine-N,N'-dimalonic acid (EDDM), 2,2'-azanediyldisuccinic acid, 2,2'-oxydisuccinic acid (ODS), ethylenediaminedisuccinic acid (EDDS), diethylenetriaminepentaacetic acid (DTPA), ethylene diamine tetraacetic acid (EDTA), 2,2'-((((1,2-dicarboxyethyl)azanediyebis(ethane-2,1-diyl))bis(oxy))disuccinic acid, and any combination thereof. Preferably the polyacid is citric acid. A PEI-citrate complex forms a stable colloidal when the ratio of protonated linear PEI to citric acid ranges from about 70:30 to 90:10 (e.g., about 70:30, about 75:25, about 80:20, about 85/15, or about 90:10). If more citric acid is desired in the complex, for example 60:40, the colloidal may become unstable. However, the colloidal can be made stable by filtering out the larger citrate complexes.

In another embodiment, the cationic polymer is chitosan. When the cationic polymer is chitosan, formation of a PEC is optional, i.e., an anionic polymer is optionally present in the composition. In some instances, chitosan with 95% or less deacetylation and/or deacetylation with quarternization (e.g., trimethylchitosan) results in a more soluble high molecular weight chitosan. Thus, it is possible to create a low soluble film durable enough to not require the formation of a PEC.

The chitosan typically has a number average molecular weight between 20,000 g/mol and 2,000,000 g/mol. The chitosan can have a number average molecular weight of 2,000,000 g/mol or less, for example, 1,750,000 g/mol or less, 1,500,000 g/mol or less, or 1,250,000 g/mol or less. Alternatively, or in addition, the chitosan can have a number average molecular weight of 20,000 g/mol or more, for example, 50,000 g/mol or more, 100,000 g/mol or more, 250,000 g/mol or more, 500,000 g/mol or more, or 1,000,000 g/mol or more. Thus, the chitosan can have a number average molecular weight bounded by any two of the aforementioned endpoints. For example, the chitosan can have a number average molecular weight between 20,000 g/mol and 2,000,000 g/mol, between 20,000 g/mol and 1,750,000 g/mol, between 20,000 g/mol and 1,500,000 g/mol, between 20,000 g/mol and 1,250,000 g/mol, between 20,000 g/mol and 1,000,000 g/mol, between 50,000 g/mol and 2,000,000 g/mol, between 100,000 g/mol and 2,000,000 g/mol, between 250,000 g/mol and 2,000,000 g/mol, between 500,000 g/mol and 2,000,000 g/mol, or between 1,000,000 g/mol and 2,000,000 g/mol.

When the antimicrobial composition optionally comprises at least one anionic polymer, which forms a PEC with the cationic polymer, the PECs can offer two important advantages to the present invention: 1) the assembly of polymers using PECs eliminates the use of chemical cross-linking agents, thereby reducing possible toxicity and other undesirable effects of the reagents; and 2) the PECs formed between a poly acid and poly base are tolerant of pH variations in the dissolution medium.

The anionic polymer can be any suitable anionic polymer that is capable of forming a PEC with the cationic polymer, such as an anionic polymer selected from a polyacrylic acid salt, a polysulfate, a polysulfonate, a polycarboxylate, a polyoxometalate, a sulfonated or carboxylated metalloporphyrin, xanthan gum, alginate, or a lignin compound (e.g., lignosulfonate, pectin, carrageenan, humate, fulvate, angico gum, gum Kondagogu (*Cochlospermum gossypium* DC), sodium alkyl naphthalene sulfonate (e.g., MORWET™), poly-γ-glutamic acid, maleic starch half-ester, carboxymethyl cellulose, chondroitin sulphate, dextran sulphate, and hyaluronic acid). The anionic polymer can be linear, branched, dendritic, graft, or present as a copolymer (e.g., block copolymer).

In preferred embodiments, the anionic polymer is a polyacrylic acid salt (PAAS). Specific examples of PAAS include polyacrylic acid alkali metal salts (e.g., polyacrylic acid sodium salt) and polyacrylic acid ammonium salts. The polyacrylic acid salt has a number average molecular weight of at least 10,000 g/mol. For example, the polyacrylic acid salt can have a number average molecular weight of 20,000 g/mol or more, e.g., 40,000 g/mol or more, 60,000 g/mol or more, 80,000 g/mol or more, 100,000 g/mol or more, 120,000 g/mol or more, or 140,000 g/mol or more.

The size and internal structure of the PEC particles are regulated by, for example, the formation process, media and structural parameters, particular mixing order, mixing ratio, PEC concentration, pH, and molecular weight. Controlling the size of the PEC particle is important because the particle size affects 1) the overall stability of the Pickering PEC; 2) the solvency of the film formed by the dispersion; and 3) the adhesive strength of the film to a substrate. The solvency and adhesiveness of the film can be tuned by controlling the size of the final PEC colloidal. Some applications might require a less soluble and more adhesive film. However, tuning these two attributes will always be constrained by the stability issue. If too much anionic polymer is used, the PEC colloidal will become too large and precipitate out.

The size of the final PEC particle can be determined by the quantity of anionic polyelectrolyte (n−) relative to the quantity of cationic polyelectrolyte (n+). If the n−/n+ ratio is high, the PEC particle will grow. However, when the cationic polymer is dosed into the anionic polymer, there is a point of accelerated growth and then a fall-off in size. The preferred method of doping is to dose the anionic polymer into the cationic polymer, even though this order of dosing cannot create the smallest particles (assuming n−/n+ is below 0.8).

The size of the PEC particle is also influenced by the mixing order. When the anionic polymer is dosed into cationic polymer, the PEC particle becomes larger. Nevertheless, there are techniques to offset this undesirable growth. First, the size of the PEC emulsion particles can be kept small by limiting the concentration of polyelectrolyte in the forming solution; in other words, work with a very dilute solution. Given that the preferred mixing order has a detrimental effect on particle size, the offsetting strategy put forth in the present invention is to work with dilute solutions, i.e., limit the concentration of the polymers and then evaporate off the excess water after the formation of the PECs. In a specific embodiment of the invention, the method prefers, but is not limited to, using a cationic polymer (e.g., polydiallyldialkylammonium salt, acryloxyalkyltrialkylammonium salt, vinylphenalkyltrialkylammonium salt, acrylamidoalkyltrialkylammonium salt, PEI, and/or chitosan) at a concentration of about 0.001 to 0.1 M (e.g., 0.005 M).

A second method of offsetting the tendency of the PEC to grow is to control the pH of the cationic polymer mixture relative to the pH of the anionic polymer mixture. For example, a lower pH of the cationic polymer (pH ~4) and high pH of the anionic polymer (pH ~10) results in a smaller particle size. Thus, the preferred, but not required, pH of the cationic polymer (e.g., polydiallyldialkylammonium salt, acryloxyalkyltrialkylammonium salt, vinylphenalkyltrialkylammonium salt, acrylamidoalkyltrialkylammonium salt, PEI, and/or chitosan) solution for creating the PEC is kept at ~4 and the anionic pH is maintained at ~10. The pH of the final PEC solution is ~4.5 and after evaporation, the pH is adjusted to ~7.4. It is believed that the lower pH of the cationic polymer fluid contributes to a smaller particle size and thus helps to offset the negative influence of dosing order and molecular weight, encouraging a larger particle size.

The antimicrobial composition should be kept at a pH near 7 in order to pass the EPA cytotoxicity test. Even a slight dissolution of the film during the test can cause leaching, and a pH much above or below 7 will kill the mammalian cells used in the test and the film will fail. Also, a pH of 7 should help ensure that the anionic polymer is maintained in an ionized form. If necessary, the pH can be adjusted by the addition of suitable acids (e.g., hydrochloric acid, sulfuric acid, citric acid, etc.) or bases (e.g., sodium hydroxide, potassium hydroxide). It is recommended that the final pH be adjusted subsequent to dispersing any organic and/or inorganic particles into the PEC.

With respect to the present invention, it is important that the PEC surface remains strongly positive. For example, if an excess quantity of anionic polymer is added (i.e., if the (n−/n+) is too high) the PEC particle charge will become negative, which would destroy the effectiveness of the antimicrobial composition, since it is believed that the antimicrobial mode of action is related to the positively charged cationic polymer(s) attracting and piercing a negatively charged microbial membrane. It is therefore important that the PEC particle charge remains positive. For the purpose of the present invention, it is recommended that (n−/n+) value does not exceed 0.3, and preferably is below 0.2.

In general, the ppm for the film thickness is determined by the amount of carrier (e.g., water) that is evaporated from the combined solution (e.g., PEC solution). When working with a very dilute concentration, the considerable excess carrier needs to be evaporated to arrive at a desirable ppm of solids in the film-forming composition.

It is an aspect of the present invention that the PECs are assembled in such a way that the PECs have an average aggregate size in solution of less than about 500 nm (e.g., less than 400 nm, less than 300 nm, less than 200 nm). In some embodiments, the aggregate size is less than about 100 nm (e.g., less than 80 nm, less than 50 nm, less than 25 nm, less than 10 nm) in diameter. The particle size and molecular weights of the associative PECs can be measured via static or dynamic light scattering.

The antimicrobial composition preferably also comprises at least one adhesion promoter that allows the composition to adhere to the surface of a substrate to form a residual self-sanitizing film that cannot be immediately washed away. In some embodiments, the residual self-sanitizing film is not covalently bound to the surface of the substrate. The adhesion promoter can, in some instances, be described as a coupling agent. The adhesion promoter typically is one or more compounds with at least one functional group that has an attractive force to the surface of a desired substrate, the at least one cationic polymer, or both. Suitable examples of an adhesion promoter include a titanate, carboxylated branched or linear PEI, a silane compound, cationic block copolymers, and other polymers that will create "sticky," reactive groups, such as acyl or carboxylic acid, and carboxylic acid derivatives. Preferably, the adhesion promoter is a carboxylated branched PEI, as it does not detract from the cationic charge of the polymers.

The titanate can be any suitable titanate that increases the composition's ability to adhere to a surface and/or enables the composition or a film formed from the composition to pass one or more of tests (i)-(v). Typically, the titanate is selected from an alkoxy titanate, a neoalkoxytitanate, an oxyacetate chelated titanate, an ethylene chelated titanate, a pyrophosphate titanate, and combinations thereof.

In preferred embodiments, the titanate is selected from titanium IV 2,2(bis 2-propenolatomethyl)butanolato, tris neodecanoato-O, titanium IV 2,2(bis 2-propenolatomethyl) butanolato, tris(dodecyl)benzenesulfonato-O, titanium IV 2,2(bis 2-propenolatomethyl)butanolato, tris(dioctyl)phosphato-O, titanium IV 2,2(bis 2-propenolatomethyl)butanolato, tris(dioctyl)pyrophosphato-O, titanium IV 2,2(bis 2-propenolatomethyl)butanolato, tris(2-ethylenediamino) ethylato, titanium IV 2,2(bis 2-propenolatomethyl)butanolato, tris(3-amino)phenylato, titanium IV 2,2(bis 2-propenolatomethyl)butanolato, tris(6-hydroxy)hexanoato-O, or any combination thereof. Typically, the titantate is titanium IV 2,2(bis 2-propenolatomethyl)butanolato, tris neodecanoato-O.

The antimicrobial composition can comprise any suitable amount of titanate to form a residual self-sanitizing film. The antimicrobial composition can comprise, for example, titanate in an amount of 0.1% weight based on monomers ("wbm") of the cationic polymer, or more, for example, 0.2% wbm or more, 0.3% wbm or more, 0.4% wbm or more, or 0.5% wbm or more. Alternatively, or in addition, the antimicrobial composition can comprise titanate in an amount of 6% wbm of the cationic polymer, or less, for example, 5% wbm or less, 4% wbm or less, 3% wbm or less, 2% wbm or less, 1% wbm or less, 0.9% wbm or less, 0.8% wbm or less, or 0.7% wbm or less. Thus, the antimicrobial composition can comprise titanate in an amount bounded by any two of the aforementioned endpoints. For example, the antimicrobial composition can comprise titanate in an amount between 0.1% wbm to 6% wbm of the cationic monomers, for example, between 0.2% wbm to 6% wbm, between 0.3% wbm to 6% wbm, between 0.4% wbm to 6% wbm, between 0.5% wbm to 6% wbm, between 0.5% wbm to 5% wbm, between 0.5% wbm to 4% wbm, between 0.5% wbm to 3% wbm, between 0.5% wbm to 2% wbm, between 0.5% wbm to 1% wbm, between 0.5% wbm to 0.9% wbm, between 0.5% wbm to 0.8% wbm, or between 0.5% wbm to 0.7% wbm, e.g., 0.6% wbm.

The adhesion promoter can be carboxylated PEI (PEI-COOH) that is either branched, linear, or a mixture of branched and linear. The PEI-COOH can be purchased commercially or prepared from PEI. For example, bromoacetic acid in water can be added to PEI in water. The resulting mixture is then stirred and then filtered to isolate the polymer and remove unreacted acid. The PEI-COOH can have any suitable molecular weight but typically has a number average molecular weight between 15,000 g/mol and 250,000 g/mol. The PEI-COOH can be used in a suitable amount that usually ranges from 0.001% to 3% by weight, including ranges with end points at 0.01%, 0.1%, 0.5%, 1%, 1.5%, 2%, and/or 2.5%. A preferred amount ranges from 0.001% to 0.01%, such as 0.001% by weight.

A silane compound, such as a silane coupling agent, can be used as the adhesion promoter. In general, a silane coupling agent has functional groups at both terminal ends that allow an organic group, such as the cationic polymer, to bond to an inorganic group, such as a substrate. The silane compound can have the formula $R-(CH_2)_n-Si-X_3$, in which R is an organofunctional group (e.g., optionally substituted linear or branched $C_1$-$C_{20}$ alkyl, optionally substituted aryl, such as phenyl or naphthyl, amino, such as $-NH(CH_2)_3NH_2$, epoxy, or methacryloxy), n is an integer from 0 to 6, and X is a hydrolyzable group (e.g., alkoxy, acyloxy, halo, or amino). Suitable examples include a trialkoxysilane and a monoalkoxysilane, in which the alkoxy is $C_1$-$C_6$ alkoxy (e.g., methoxy, ethoxy, propoxy, isopropoxy, butoxy, or a combination thereof), a dipodal (branched) silane with two alkoxy-silane branches, a cyclic azasilane, a vinyl silane, an acryloxy silane, an epoxysilane, and an aminosilane, or any combination thereof. Specific examples of silane compounds include methyltrimethoxysilane, methyltriethoxysilane, isobutyltrimethoxysilane, n-octytriethoxysilane, phenyltrimethoxysilane, vinyltrichlorosilane, vinyltris(β-methoxyethoxy)silane, vinyltriethoxysilane, vinyltrimethoxysilane, 3-metacryloxypropyl-trimethoxysilane, β-(3,4-epoxycyclohexyl)-ethyltrimethoxysilane, γ-glycidoxypropyl-trimethoxysilane, γ-glycidopropyl-methylidiethoxysilane, N-β(aminoethyl)-γ-aminopropyl-trimethoxysilane, N-β(aminoethyl)-γ-aminopropyl-methyldimethoxysilane, 3-aminopropyl-triethoxysilane, and N-phenyl-γ-aminopropyl-trimethoxysilane, or a combination thereof.

The adhesion promoter can also be a cationic block copolymer, such a high molecular weight polyethylene-based copolymer with basic or acidic adhesive groups, such as an amino and/or hydroxy. Commercial products of this type include BYK™ 4500, BYK™ 4510, BYK™ 4509, BYK™ 4512, and BYK™ 4513, which are available from BYK Chemie GmbH (Wesel, Germany). Suitable amounts of the block copolymer range from 0.001% to 5% by weight, including ranges with end points at 0.01%, 0.1%, 0.5%, 1%, 1.5%, 2%, 2.5%, 3%, 3.5%, 4%, or 5%. A preferred amount ranges from 0.5% to 2%, such as 1% by weight.

The adhesion promoter can also be a polymer that either naturally has or has been modified to have "sticky," reactive groups, such as an acyl group, a carboxylic acid, a carboxylic acid derivative, a sulfur-containing moiety (e.g., thio), an amino group, hydroxyl, and/or a halo-containing group. The polymer itself is any suitable moiety, preferably without a charge, such as polyethylene, polypropylene, poly(ethylene-vinylacetate), polyester, polyurethane, polyamide, polyvinyl acetate, polyvinyl alcohol, polyvinyl butyral, polyvinyl chloride, polyvinyl ether, or a combination thereof. Suitable amounts of the polymer range from 0.001% to 3% by weight, including ranges with end points at 0.01%, 0.1%, 0.5%, 1%, 1.5%, 2%, and/or 2.5%. A preferred amount ranges from 0.5% to 2%, such as 1% by weight.

In some embodiments, the antimicrobial composition comprises organic and/or inorganic particles that are photocatalytically active in visible light and can be any suitable organic-based (e.g., graphene or graphitic carbon nitride (g-$C_3N_4$)) and/or inorganic-based particles that are photocatalytically active in visible light (e.g., between 390 to 700 nm). Organic and/or inorganic particles that are photocatalytically active generate reactive oxygen species that are able to destroy pathogenic microbes (e.g., kills *C. difficile*, bacteria and/or viruses, including avian flu and SARS) that augments the disinfectant property of the composition. Generally, the organic and/or inorganic particles that are photocatalytically active in visible light are selected from graphene, g-$C_3N_4$, a transition metal oxide, a transition metal sulfide, a transition metal selenide, a dye sensitizer, a conjugated polymer, a noble metal, or a mixture thereof. A mixture of particles means that two or more different kinds of particles are present in the antimicrobial composition, whereas in a multijunction composite, various components of the composite are tightly coupled to assure electron transfer, and minimize recombining of holes.

As used herein, the term "particle" includes sphere-like particles (e.g., spheres) and other shapes, such as platelets, rods, cubes, and flakes or combinations of various shapes and morphologies.

Graphene is an allotrope of carbon, in which carbon atoms are bonded to one another in sheet form that is one atom thick. The graphene can optionally be functionalized with an oxygen- and/or nitrogen-containing group. An analog of graphite is graphitic carbon nitride (g-$C_3N_4$), which is photocatalytic.

The transition metal oxide, sulfide, and selenide can be any suitable compound comprising at least one metal atom and at least one anion of oxygen, sulfur, or selenium that has an oxidation state of –2. In some aspects, the transition metal oxide is selected from the group consisting of silicon dioxide (including fumed silica, amorphous silica, precipitated silica, hydrophilic silica, and hydrophobic silica), titanium dioxide, zinc oxide, iron oxide, aluminum oxide, cerium oxide, zirconium oxide, and a combination thereof; the transition metal sulfide is selected from cadmium sulfide, molybdenum disulfide, tungsten sulfide, silver sulfide, zinc sulfide, selenium sulfide, iron disulfide, nickel sulfide, ruthenium sulfide, cobalt sulfide, and a combination thereof; and/or the transition metal selenide is selected from cadmium selenide, copper selenide, copper geranium selenide, copper indium gallium selenide, copper titanium selenide, indium selenide, manganese diselenide, titanium selenide, tungsten diselenide, silver selenide, disilver selenide, digold triselenide, zinc sulfide, iron selenide, nickel selenide, ruthenium selenide, cobalt selenide, and a combination thereof.

Tungsten doping, as well as other metallic doping, has been demonstrated to inhibit charge recombination and improve photocatalytic activity of photocatalysts (Rozenberg et al., *Prog Polym Sci*, 2008, 33: 40-112). In certain embodiments, the transition metal oxide/sulfide/selenide particle can be doped with a suitable metal, such as tungsten, nitrogen, or a combination of tungsten and nitrogen.

In one embodiment, the transition metal oxide is titanium dioxide ($TiO_2$). The $TiO_2$ particles can be obtained from any suitable mineral form of $TiO_2$. For example, the $TiO_2$ particles can maintain an anatase crystalline structure, a brookite crystalline structure, or a rutile crystalline structure. In preferred embodiments, the $TiO_2$ maintains an anatase crystalline structure.

The $TiO_2$ particles can be any suitable structure type. Typically, the $TiO_2$ particles are $TiO_2$ nanoparticles ("NP"). The $TiO_2$ nanoparticles can be synthesized by any suitable process. For example, the $TiO_2$ nanoparticles can be liquid-synthesized or gas-synthesized. In preferred embodiments, the $TiO_2$ nanoparticles are liquid-synthesized, since a liquid synthesis tends to create soft agglomerates, which make it easier to disperse the $TiO_2$. An illustrative $TiO_2$ nanoparticle is a 25 nm, anatase, liquid-phase synthesized $TiO_2$ nanoparticle doped with tungsten, which can be purchased from Nanostructured & Amorphous Materials, Inc. (Houston, Tex.).

In a specific example of functionalizing $TiO_2$ particles, W-doped, liquid synthesized $TiO_2$ (20 nm) is calcined with urea at 400° C. for 1 hour, which produces a poly(amino-tri-s-triazine) polymer covalently attached to the $TiO_2$ particles. Next, the WlN-doped $TiO_2$ particles are milled along with powdered urea. The hard material created from calcination is ground into powder so that it can be placed, along with urea, into a planetary ball mill. The milling spec is to mill at 300 rpm for 30 minutes with 10% urea and balls weighing 10 times the weight of the $TiO_2$. After 30 minutes, the milling drum is three-quarters filled with 200 ml of $H_2O$ and milled an additional 5 minutes to capture and disperse the $TiO_2$ nanoparticles. The contents are then put into a beaker and mixed under 150W UV light for 1 hour. The highly dispersed nanopowder is then available to be added to the antimicrobial composition. It is important to note that the nanopowder is highly dispersed in water, which keeps it in a non-agglomerated nano state. As such, the functionalization process described herein enables the $TiO_2$ to be dispersible in water, wherein $TiO_2$ is typically only dispersible in alcohol. Creating such a stable nano-dispersion without a surfactant means that when the particles are dispersed into a cationic polymer solution or the PEC, the particles will not be contaminated with a surfactant that could possibly dampen their ability to respond to visible light.

The high-energy milling of $TiO_2$ particles achieves two things: 1) it de-agglomerates the powder to create nanoparticles; and 2) the urea double dopes the particles with nitrogen, and in particular, any new exposed particle facets are doped as the high-energy milling breaks up agglomerates and aggregates. Essentially, it is believed that the milling forces nitrogen into the pores and covers facets that were not previously exposed during the calcination process. Following calcination with urea and milling with urea, the $TiO_2$ nanoparticles are irradiated with a 150 watt UV light. Without wishing to be bound by any theory, it is believed that UV irradiation improves the visible light responsiveness of $TiO_2$ nanoparticles because of the introduction of hydroxyl groups on to the surface of the $TiO_2$ nanoparticles. This is one explanation for why the particles are easily dispersed in water. The ability of the functionalized nanoparticles to degrade methylene blue was tested, and it was observed that the sum of all four functionalization steps significantly degraded the dye within 90 minutes.

Lastly following calcination, milling, washing, and light irradiation, the particles can be dye-sensitized. The theory and practice of using dye to enhance the visible-light sensitivity of a transition metal oxide particle (e.g., $TiO_2$) is central to "dye-sensitized solar cell" (DSSC) technology. DSSCs have been attracting considerable attention in recent years owing to their comparatively low cost and high efficiency. A DSSC is essentially a photo-electrochemical system, in which light harvesting is accomplished by dye molecules that are adsorbed on the surface of the oxide nanostructures that form the photo-electrode film. Surface sensitization of a wide band gap semiconductor photocatalyst, such as $TiO_2$, via chemisorbed or physisorbed dyes can increase the efficiency of the excitation process and expand the wavelength range of excitation for the transition metal oxide particle (e.g., $TiO_2$). This occurs through excitation of the sensitizer that can inject either a hole or, more commonly, an electron into the particle. Highly efficient charge injection is observed when a monolayer of a dye is dispersed on a photocatalyst with a high surface area. This sensitization increases the range of the wavelength response of the photocatalyst, which is important for it to operate under natural sunlight. The electron injection and back electron-transfer rates from the dye to the transition metal oxide particle (e.g., $TiO_2$) depend on the nature of the dye molecule, the properties of the transition metal oxide particle (e.g., $TiO_2$), and the interactions between the dye and the transition metal oxide particle. The dye is any suitable compound, such as fluorescein, fluorescein isothiocyanate, a cyanine, a merocyanine, a hemicyanine, a perylene, a xanthene, a porphyrin (e.g., tetraphenylporphyrin), a phthalocyanine (e.g., copper phthalocyanine), a polyene, a polythiophene, a coumarin (e.g., NKX-2677, NKX-2587, NKX-2697, NKX-2753, NKX-2586, or NKX-2311), and a ruthenium-based dye (e.g., $(Bu_4N)_2[Ru(dcbpyH)_2(NCS)_2]$ (N719), $(Bu_4N)_2[Ru(dcbpy)_2(NCS)_2]$, cis-di(thiocyanato) bis(2,2'-bipyridyl-4,4'-dicarboxylate) ruthenium(II) (N3), tri(thiocyanato)-2,2',2"-terpyridyl-4,4',4"-tricarboxylate)ruthenium(II) (black dye), K8, K9, K19, and Z907). In a specific embodiment of the invention, N719 dye is applied by mixing calcinated/milled/UV light functionalized transition metal oxide particles (e.g., $TiO_2$) for 1 hour in the dark with a 0.5 mM mixture of N719 dye in ethanol. Other dyes can also be used. The functionalized particles are decanted, centrifuged, and added back to water.

In any of the embodiments described herein, the $TiO_2$ particles are doped with tungsten and nitrogen and are hydrolyzed under ultraviolet (UV) light. The resulting particles are visible light-responsive $TiO_2$ particles that are effective as an antimicrobial agent, particularly when such particles are embedded in a film formed from an antimicrobial composition of the present invention. Accordingly, the invention provides a method of killing microbes on a surface (e.g., disinfecting a surface, providing a residual self-sanitizing film, or both) comprising applying to the surface an antimicrobial composition comprising (i) visible light-responsive $TiO_2$ particles that are doped with tungsten and nitrogen, (ii) at least one adhesion promoter (e.g., a titanate, a carboxylated branched PEI), and (iii) a carrier. The adhesion promoter is as described herein, and the carrier can be, e.g., water, alcohol, or a combination of water and alcohol, as described herein.

Without wishing to be bound by any particular theory, the electronic structure of $TiO_2$ is characterized by a filled valence band and an empty conduction band. The band gap energy is excited and an electron is promoted from the valence band to the conduction band and an electron-hole pair is generated. This electron hole reacts with water to generate active oxygen such as hydroxyl radicals, sometimes referred to as reactive oxygen species (ROS). The positive hole of $TiO_2$ breaks the water molecule apart to form hydrogen gas and hydroxyl radicals. The negative electron reacts with oxygen molecules to form a super-oxide anion ($O_2^-$). Super oxide anions further react with water molecules to generate hydroxyl radical peroxide (•OOH) and hydrogen peroxide ($H_2O_2$). Each •OH, $O_2^-$, •OOH, and $H_2O_2$ can react with pathogenic microbes and destroy their cell structure.

In addition, the electron holes themselves can directly react with the microbial cell wall, cell membrane, and cell components. In microzymes and bacilli, intracellular coenzyme A (CoA) is oxidized by $TiO_2$ such that the CoA dimer loses its activity, which causes the respiration of the cell to stop and finally results in microbial death. During this process, the electron shift between the killed cell and $TiO_2$ is passed through CoA. Therefore, the content of CoA decreases and the CoA dimer increases.

The dye sensitizer is any suitable compound, such as fluorescein, fluorescein isothiocyanate, a cyanine, a merocyanine, a hemicyanine, a perylene, a xanthene, a porphyrin (e.g., tetraphenylporphyrin), a phthalocyanine (e.g., copper phthalocyanine), a polyene, a polythiophene, a coumarin (e.g., NKX-2677, NKX-2587, NKX-2697, NKX-2753, NKX-2586, or NKX-2311), and a ruthenium-based dye (e.g., $(Bu_4N)_2[Ru(dcbpyH)_2(NCS)_2]$(N719), $(Bu_4N)_2[Ru(dcbpy)_2(NCS)_2]$, cis-di(thiocyanato)bis(2,2'-bipyridyl-4,4'-dicarboxylate) ruthenium(II) (N3), tri(thiocyanato)-2,2',2"-terpyridyl-4,4',4"-tricarboxylate)ruthenium(II) (black dye), K8, K9, K19, and Z907).

The organic and/or inorganic photocatalytic particles can include a conjugated polymer that conducts. A suitable conjugated polymer includes polypyrrole (Ppy), poly(3-hexylthiophene) (P3HT), polycarbazole, polyindole, polyazepine, polyaniline, polyfluorene, polyphenylene, polypyrene, polyazulene, polynaphthalene, polythiophene (Ptp), poly(3,4-ethylenedioxythiophene), poly(p-phenylene sulfide), polyacetylene, poly(p-phenylene vinylene), and any combination thereof. The conjugated polymer can be incorporated into a nanocomposite that is specifically designed to react with ordinary room lighting to create reactive oxygen species (ROS). The ROS destroy difficult-to-kill spore-like microbes, such as C. difficile and fungi. The ROS also oxidize microbial debris, thus performing an ongoing cleaning function. In a particular embodiment, the photocatalytic nanocomposite is comprised of a multi-junction composite comprising: $WTiO_2$/CN heterojunction/Ppy, in which $WTiO_2$ is tungsten-doped $TiO_2$ nanoparticles, as described herein, CN is graphitic carbon nitride (g-$C_3N_4$), and Ppy is polypyrrole.

Historically, most photocatalytic materials have been designed around various metal sulfides and metal oxides rather than polymers. Titanium dioxide ($TiO_2$) has been the metal oxide of choice because it is readily available, inexpensive, stable, non-toxic, and highly reactive in the ultraviolet (UV) light spectrum. The inventors wanted to go beyond the use of $TiO_2$ because the goal was to create a photocatalytic material that would be reactive in ordinary room lighting. As $TiO_2$ has a wide band gap (3-3.2 eV), it only absorbs light in the UV spectrum, none of which is present in indoor room lighting. Thus, the present invention provides a photocatalytic nanocomposite that is based upon polymers, i.e., with no or very limited use of metals. Such nanocomposite is likely to be less toxic for humans and the environment and has no anionic charge to off-set the cationic charge when incorporated in a cationic polymer-containing residual self-sanitizing film, as described herein. In a nano-composite based more on polymers, $WTiO_2$ in the $WTiO_2$/CN heterojunction/Ppy multi-junction composite is replaced with an acid-modified or protonated graphitic carbon nitride ($g$-$C_3N_4$). The protonation of CN gives the CN a band gap with valance and conductive bands that are quite close to $TiO_2$. The inventors have developed several techniques to create the protonated CN, which is termed acidified carbon nitrate (ACN), and then strongly couple the protonated CN to the heterogeneous CN and a conjugated polymer (such as polypyrrole (Ppy), poly(3-hexylthiophene) (P3HT), polythiophene (Ptp), and the like), thereby resulting in a photocatalytic composite specifically engineered to capture low level indoor light. This method is explained in detail in U.S. Provisional Patent Application 62/367,981 and the inventors' concurrently filed provisional patent application, the entire contents of which are incorporated herein by reference.

The benefits of this new, polymer-based, photo-reactive material include one or more of the following: (i) maximum light harvesting with multi-junction band slicing, (ii) maximum photon utilization by using materials with appropriate band edges, sequencing the assembly and tight coupling to foster rapid electron transport, and minimizing electron-hole recombination, (iii) assembly using a low-cost, easily scalable manufacturing process that does not use toxic chemicals or generate waste, and that creates a Nano, mesoporous material with an exceedingly high surface area that creates a mixed morphology stable dispersion of micro, nano, and crystalline particles and platelets that maximizes the optical path of the incident light and preserves all "unseen" nano/crystalline particles and platelets.

The organic and/or inorganic photocatalytic particles can include a noble metal, such as ruthenium, rhodium, palladium, silver, osmium, iridium, platinum, gold, or a mixture thereof. In some embodiments, the noble metal is platinum.

The average diameter of the organic and/or inorganic particles that are photocatalytically active in visible light is not particularly limited and can range from 5 nm to 1,000 nm. The organic and/or inorganic particles can have an average diameter of 1,000 nm or less, for example, 750 nm or less, 500 nm or less, 250 nm or less, or 100 nm or less. Alternatively, or in addition, the organic and/or inorganic particles can have an average diameter of 5 nm or more, for example, 10 nm or more, or 15 nm or more. Thus, the organic and/or inorganic photocatalytic particles can have an average diameter bounded by any two of the aforementioned endpoints. For example, the organic and/or inorganic photocatalytic particles can have an average diameter of 5 nm to 1,000 nm, 5 nm to 750 nm, 5 nm to 500 nm, 5 nm to 250 nm, 5 nm to 100 nm, 10 nm to 100 nm, or 15 nm to 100 nm.

The antimicrobial composition can comprise any suitable amount of organic and/or inorganic photocatalytic particles to form a residual self-sanitizing film. The antimicrobial composition can comprise organic and/or inorganic photocatalytic particles in an amount of 1% weight based on monomers ("wbm") of the cationic monomers, or more, for example, 1.5% wbm or more, 2% wbm or more, 2.5% wbm or more, 3% wbm or more, 4% wbm or more, or 5% wbm or more. Alternatively, or in addition, the antimicrobial composition can comprise organic and/or inorganic particles in an amount of 20% wbm or less of the cationic polymer, or less, for example, 18%% wbm or less, 15% wbm or less, 12% wbm or less, 10% wbm, 9% wbm or less, 8% wbm or less, 7% wbm or less, 6% wbm or less, or 5% wbm or less. Thus, the antimicrobial composition can comprise organic and/or inorganic particles in an amount bounded by any two of the aforementioned endpoints. For example, the antimicrobial composition can comprise organic and/or inorganic particles in an amount between 1% wbm to 20% wbm of the cationic monomers, for example, between 1% wbm to 15% wbm, between 1% wbm to 10% wbm, between 1% wbm to 7% wbm, between 1% wbm to 6% wbm, between 1% wbm to 5% wbm, between 4% wbm to 20% wbm, between 5% wbm to 15% wbm, between 4% wbm to 8% wbm, or between 5% wbm to 8% wbm.

In an aspect of the invention, an antimicrobial composition comprises at least one organic and/or inorganic particle that is photocatalytically active in visible light, at least one adhesion promoter, and a carrier. The organic and inorganic photocatalytic particles, adhesion promoter, and carrier are described herein. A film formed from an antimicrobial composition comprising a photocatalytic particle kills microbes under the conditions of the modified protocol for JIS Z 2801 (2006 version, which was updated in 2010). For example, an antimicrobial composition comprising at least one organic and/or inorganic particle that is photocatalytically active in visible light kills at least 90% (e.g., at least 92%, at least 94%, at least 96%, at least 97%, at least 98%, at least 99%) of a log 4 population of *Clostridium difficile* bacteria, fungus, or yeast within 24 hours of contact. As such, the composition can be used in accordance with any of the methods described herein to kill microbes on a surface.

In some embodiments, the antimicrobial composition comprises a salt, which can affect the ability of the cationic polymer to adsorb to the surface of a substrate and create a film. Without wishing to be bound by any theory, it is believed that high salt concentrations cause conditions similar to the interactions experienced by a polymer in a favorable solvent. Polyelectrolytes, while charged, are still mainly non-polar with carbon backbones. While the charges on the polymer backbone exert an electrostatic force that drives the polymer into a more open and loose conformation, if the surrounding solution has a high concentration of salt, then the charge repulsion will be screened. Once this charge is screened, the polyelectrolyte will act as any other non-polar polymer would in a high ionic strength solution and begin to minimize interactions with the solvent, which can lead to a much more clumped and dense polymer deposited onto the surface and improved adsorption or adhesion.

The salt is any inorganic salt, such as any salt containing a cation of a Group I metal (lithium, sodium, potassium, rubidium, or cesium), a Group II metal (beryllium, magnesium, calcium, strontium, or barium), ammonium, or aluminum. The counter anion can be a halide, carbonate, bicarbonate, sulfate, thiosulfate, phosphate, nitrate, nitrite, acetate, bromate, chlorate, iodate, etc. Specific examples of salt include lithium bromide, lithium chloride, lithium iodate, lithium iodide, lithium hydroxide, lithium sulfate, lithium phosphate, sodium bromide, sodium chloride, sodium acetate, sodium bicarbonate, sodium bisulfate, sodium bromate, sodium chlorate, sodium hydrosulfide, sodium hydroxide, sodium hypophosphite, sodium iodate, sodium iodide, potassium acetate, potassium bicarbonate, potassium bromate, potassium bromide, potassium chloride, potassium carbonate, potassium chlorate, potassium hydroxide, potassium iodide, potassium phosphate, potassium thiosulfate, rubidium bromide, rubidium chloride, rubidium fluoride, rubidium iodide, rubidium nitrate, rubidium sulfate, cesium bromide, cesium chloride, cesium carbonate, cesium nitrate, beryllium nitrate, beryllium sulfate, magnesium acetate, magnesium bromide, magnesium chloride, magnesium iodate, magnesium iodide, magnesium nitrate, magnesium phosphate, magnesium sulfate, calcium acetate, calcium bromide, calcium chloride, calcium iodide, calcium iodate, calcium nitrite, calcium nitrate, calcium phosphate, calcium sulfate, strontium bromide, strontium chloride, strontium hydrogen phosphate, strontium iodide, strontium nitrate, strontium sulfate, barium acetate, barium bromide, barium chloride, barium iodide, barium nitrate, barium phosphate, barium sulfate, barium thiosulfate, ammonium acetate, ammonium bicarbonate, ammonium bromide, ammonium chloride, ammonium nitrate, aluminum chloride, aluminum phosphate, and any combination thereof. In some embodiments, the salt is a Group I-halide salt, such as sodium chloride or potassium chloride.

The antimicrobial composition can comprise any suitable amount of salt, such as 0.01 M to 0.1 M, including any combination of endpoints at, e.g., 0.01 M, 0.02 M, 0.03 M. 0.04 M, 0.05 M, 0.06 M, 0.07 M, 0.08 M, 0.09 M, and 0.1 M. In a specific example, the antimicrobial composition comprises 0.01 M to 0.05 M salt.

If desired, the cationic polymer can be blended with one or more non-electrolyte (nonionic) polymers. A suitable non-electrolyte (nonionic) polymer preferably is water soluble and includes, for example, a polyacrylamide, a polyamine, a polyamidoamine, polyethylene glycol, polyvinyl pyrrolidone, polyvinyl alcohol, and a polyacrylate (e.g., poly(methyl)methacrylate), or any combination thereof.

The antimicrobial composition comprises a carrier. The carrier can be any suitable carrier that evaporates once the composition is applied to a desired surface. In general, the carrier is selected from an alcohol, water, or a combination thereof. In some embodiments, the carrier comprises a combination of water and alcohol. A suitable alcohol includes methanol, ethanol, n-propanol, iso-propanol, n-butanol, sec-butanol, and t-butanol, or a combination thereof. In preferred embodiments, the carrier comprises ethanol (e.g., the carrier is a combination of ethanol and water). When a combination of alcohol and water is used as the carrier, the ratio of alcohol:water preferably ranges from 10:90 to 99:1 (e.g., 10:90, 20:80, 30:70, 40:60, 50:50, 60:40, 70:30, 80:20, 90:10, 95:5, and 99:1). In certain embodiments, the alcohol:water ratio ranges from 70:30 to 80:20.

In general, the antimicrobial composition does not comprise a germicidal small molecule compound (i.e., non-polymer) or antimicrobial metal, including those conventional germicidal agents that are EPA-registered, because such components have a material effect on the composition. EPA-approved germicidal agents that can be excluded from the composition include, for example, glutaral, halazone, hexachlorophene, nitrofurazone, nitromersol, povidone-iodine, thimerosol, $C_1$-$C_5$-parabens, hypochlorite salts, clofucarban, clorophen, poloxamer iodine, phenolics, mafenide acetate, aminacrine hydrochloride, quaternary ammonium salts, oxychlorosene, metabromsalan, merbromin, dibromsalan, glyceryl laurate, sodium and/or zinc pyrithione, (dodecyl)(diethylenediamine)glycine, (dodecyl)(aminopropyl) glycine, a phenolic compound, (e.g., m-cresol, o-cresol, p-cresol, o-phenyl-phenol, 4-chloro-m-cresol, chloroxylenol, 6-n-amyl-m-cresol, resorcinol, resorcinol monoacetate, p-tert-butylphenol and o-benzyl-p-chlorophenol), alkaline glutaraldehyde, and a quaternary ammonium salt (e.g., N-(higher) $C_{10}$-$C_{24}$-alkyl-N-benzyl-quaternary ammonium salts that comprise water-solubilizing anions such as halide, e.g., chloride, bromide and iodide; sulfate, and methosulfate, and the heterocyclicimides such as the imidazolinium salts). Suitable quaternary ammonium compounds are described in U.S. Pat. No. 8,067,403 and include: benzalkonium chlorides (e.g., benzalkonium chloride), substituted benzalkonium chlorides (e.g., alkyl dimethyl benzyl ammonium chloride), dual quaternary ammonium compounds (e.g., contain an equal mixture of alkyldimethyl benzyl ammonium chloride and alkyl dimethyl ethylbenzyl ammonium chloride), twin or dual chain quaternary ammonium compounds, such as dialkylmethyl amines (e.g., didecyl dimethyl ammonium chloride or dioctyldimethyl ammonium chloride), and mixtures of fourth generation quaternary ammonium compounds with second-generation quaternary ammonium compounds (e.g., didecyl dimethyl ammonium chloride with alkyl dimethyl benzyl ammonium chloride). In an embodiment, the germicide is at least one member selected from the group consisting of sodium hypochlorite, chloride, chlorine dioxide, sodium chloride, potassium persulfate, potassium permanganate, silver nitrate, chlordexidine, hexachlorophene, hydrogen peroxide, acetic acid, peracetic acid, betadine, povidone iodine, formaldehyde, glutaraldehyde, benzalkonium chloride, triclosan, boric acid, phenol, cresylic acid, thymol, and polyhexamethylbiguanide.

However, if desired, one or more additional chemical germicidal agents, such as those agents described above, can be added to any of the foregoing embodiments of the antimicrobial composition. This option provides an additional chemical killing mechanism to further enhance the antimicrobial activity of the antimicrobial composition. When one or more germicidal agents are incorporated into the antimicrobial composition, the agents are entrapped in the antimicrobial residual self-sanitizing film and are incrementally released when the coated surface comes into contact with moisture. When the film is exposed to larger amounts of water, such as when the surface is moistened by wiping, food residues, or dishwater, this can lead to the release of increased amounts of the germicide. Thus, it is important that whatever germicidal agents are used, the agents must not be toxic to humans, nor should they make the film tacky, hazy or in any way detract from the appearance of the surfaces to which they are applied. The germicidal agents are typically added in lower concentrations. Accordingly, such additives preferably comprise between 0.001% and 5% weight based on monomers ("wbm") of the cationic polymer.

In certain embodiments, the antimicrobial composition consists essentially of or consists of a polydiallydimethylammonium halide, a polyethylenimine-based polymer, an anionic polymer, at least one adhesion promoter (e.g., a titanate, a carboxylated branched PEI), optionally organic and/or inorganic particles that are photocatalytically active in visible light, and a carrier, each component of which is described herein. In some aspects of this embodiment, the organic and/or inorganic particles that are photocatalytically active in visible light are present in the composition. In certain embodiments, the antimicrobial composition consists essentially of or consists of a polydiallydimethylammonium halide, a polyethylenimine-based polymer, at least one adhesion promoter, optionally an anionic polymer, optionally organic and/or inorganic particles that are photocatalytically active in visible light, and a carrier, each component of which is described herein. In certain embodiments, the antimicrobial composition consists essentially of or consists of a polydiallydimethylammonium halide, at least one adhesion promoter (e.g., a titanate, a carboxylated branched PEI), organic and/or inorganic particles that are photocatalytically active in visible light, and a carrier, each component of which is described herein.

Another aspect of the invention is an antimicrobial composition comprising a polyethylenimine-based polymer, optionally a second cationic polymer selected from a polydiallyldialkylammonium salt, a poly(acrylamide-co-diallyldialkylammonium halide), chitosan, or a combination thereof, optionally a polyacid, optionally at least one adhesion promoter, and a carrier. The polyethylenimine-based polymer typically is linear or branched polyethylenimine (PEI), as described herein, but preferably is linear PEI that is not chemically or structurally modified.

In some instances, the second cationic polymer is absent. In other instances, the second cationic polymer is a polydiallyldialkylammonium salt that is a polydiallyldimethylammonium halide (e.g., polydiallyldimethylammonium chloride and/or polydiallyldimethylammonium fluoride). In an embodiment, the second cationic polymer is a poly(acrylamide-co-diallyldialkylammonium halide), such as poly(acrylamide-co-diallyldimethylammonium chloride). In other embodiments, the second cationic polymer is chitosan.

The polyacid and at least one adhesion promoter are as described herein.

The carrier used in the composition is any suitable carrier, as described herein (e.g., water, propanol, iso-propanol, and/or ethanol). Typically, the composition will comprise a blend of 20% to 80% by volume of various blends of alcohol with the balance made up with water. In order to increase the virucidal action, between 3% and 10% of various blends of diols, preferably those with a chain length of from 3 to 5 carbon atoms, such as a propanediol (1,2-propanediol and 1,3-propanediol) or butanediols (1,3-butanediol), can be added to the composition. Preferably the diol is 1,2-propanediol and/or the alcohol is ethanol.

A proton donor can be added to the composition in a suitable amount (e.g., about 0.015 to about 1 percent of the total weight of the alcohol, including about 0.05 to about 1 percent, about 0.08 to about 0.8 percent, about 0.1 to about 0.8 percent). The proton donor is any suitable compound, such as hydrochloric acid, nitric acid, phosphoric acid, phosphonic acid, boric acid, sulfuric acid, adipic acid, benzene 1,3,5 tricarboxylic acid, chlorosuccinic acid, cholinechloride, cis-aconitic acid, citramalic acid, citric acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, lactic acid, maleic acid, malic acid, malonic acid, nitrilotriacetic acid, oxalacetic acid, oxalic acid, phytic acid, p-toluenesulfonic acid, salicylic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane, 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxo-glutaric acid, dl-glyceric acid, 2,5 furandicarboxylic acid, or mixtures thereof. Preferably the proton donor is citric acid, tartaric acid, malonic acid, and/or malic acid. More preferably, the proton donor is citric acid.

If desired, the composition can contain other components that include, for example, propylene glycol, a thickening agent (e.g., polyacrylic acid), a humectant (e.g., glycerine, aloe vera), an essential oil (e.g., tea tree oil), fruit extract, fragrance (e.g., carbomer, aminomethyl propanol, isopropyl myristate, tocopheryl acetate), and/or dye (e.g., blue 1, red 33, yellow 5). Depending on the carrier, polymers used, and presence of additional components, the composition can be in any desirable formulation, including a liquid, a cream, a gel, or a foam.

In a specific example, the composition comprises non-chemically modified linear PEI, polyDADMAC, optionally citric acid, a carboxylated branched PEI, and a water/alcohol carrier.

In an embodiment, the polyethylenimine-based polymer and second cationic polymer form a crystalline miscible blend that results in a stable dispersion in the carrier. A miscible blend provides a clear crystalline solution that is stable, i.e., from which there is no precipitation or fall-out. A miscible blend is different than a PEC. In addition, without wishing to be bound by any theory, it is believed that the crystalline nature of the polymers in the blend have a greater surface area and are able to provide more of an interface between the cationic polymer and microbial pathogens, both in solution and as a film.

The crystalline miscible blend can be prepared by any suitable method. In a specific example, a miscible blend of non-chemically modified linear PEI and other cationic polymers can be prepared as follows. An appropriate amount of water/PEI dispersion (e.g., about 4000 ppm PEI) is heated to a temperature that is slightly above the glass transition temperature of PEI (e.g., at least 1° C. above the glass transition temperature, at least about 2° C. above the glass transition temperature, at least about 3° C. above the glass transition temperature, at least about 4° C. above the glass transition temperature, at least about 5° C. above the glass transition temperature; including a temperature that ranges from 65-80° C. or from 68-78° C. or from 70-75° C. or about 70° C., about 72° C., or about 74° C.). Next, an appropriate amount of a second cationic polymer (e.g., polyDADMAC) solution with a lower pH (e.g., a pH of about 5-6, including a pH of about 5, a pH of about 5.5, or a pH of about 6), is added. This lower pH further helps to ensure that the PEI will remain in a solution state. After vigorous mixing, the solution is cooled to room temperature. Next, an appropriate amount (e.g., between 25 and 100 ppm) of an adhesion promoter (e.g., carboxylated branched PEI) is added. Carboxylated branched PEI is very basic, which will raise the pH of the solution. The pH should be adjusted back to 6.5 so that the linear PEI does not solidify. Next, the solution is reheated to a temperature that is slightly above the glass transition temperature of PEI (e.g., at least 1° C. above the glass transition temperature, at least about 2° C. above the glass transition temperature, at least about 3° C. above the glass transition temperature, at least about 4° C. above the glass transition temperature, at least about 5° C. above the glass transition temperature; including a temperature that ranges from 65-80° C. or from 68-78° C. or from 70-75° C. or about 72°, or about 75° C.). While vigorously stirring the blend, an appropriate amount of alcohol is drizzled in. The blend is continuously stirred while cooling to room temperature. The room temperature solution is then stirred for an additional 24 hours.

The PEI-containing composition can have one or more bactericidal, virucidal, and/or germicidal properties and can, if desired, be used as an antimicrobial composition, in particular as a hand sanitizer, in accordance with the tests, substrates, and/or methods described herein. Accordingly, provided is a method of disinfecting a surface comprising applying to the surface a composition comprising a polyethylenimine-based polymer, optionally a second cationic polymer selected from a polydiallyldialkylammonium salt, a poly(acrylamide-co-diallyldialkylammonium halide), chitosan, or a combination thereof, optionally a polyacid, optionally at least one adhesion promoter, and a carrier. In an aspect of this method, a composition comprising non-chemically modified, linear PEI, optionally a polyacid, and a carrier comprising water and alcohol is used as a hand sanitizer that is particularly effective against non-enveloped viruses.

Because linear PEI is pH- and temperature-sensitive, special techniques were developed to create a stable, crystal clear, non-sticky, hand sanitizer blend comprising a linear PEI colloidal dispersion. In a specific example, a method of preparing a hand sanitizer composition includes the following steps: At room temperature, an appropriate amount of linear PEI in water was stirred vigorously to create a PEI dispersion. Under vigorous stirring, the PEI in the dispersion was then protonated with an appropriate acid, thereby bringing the pH to 6 and resulting in a clear liquid. The clear liquid was then brought to a temperature that is slightly above the glass transition temperature of PEI (e.g., at least 1° C. above the glass transition temperature, at least about 2° C. above the glass transition temperature, at least about 3° C. above the glass transition temperature, at least about 4° C. above the glass transition temperature, at least about 5° C. above the glass transition temperature; including a temperature that ranges from 65-80° C. or from 68-78° C. or from 70-75° C. or about 70° C., about 72° C., or about 74° C.). An appropriate amount of alcohol was then drizzled in so as to maintain the temperature of the clear liquid at about 65° C. The clear hand sanitizer mixture was taken off the heat to avoid excessive alcohol evaporation and then stirred for several hours (e.g., at least 2 hours, at least 3 hours, at least 4 hours, or at least 5 hours) while covered.

An antimicrobial composition of the present invention meets or exceeds at least one of the following antimicrobial tests:

(i) a germicidal spray test according to ASTM E1153 that meets the EPA requirement of log 3 reduction for viruses and a log 5 reduction for bacteria, (ii) a suspension test according to ASTM E1052-96 (2002) or ASTM E2315 (2016), (iii) a film formed from the composition kills (iii-a) at least 95% of log 5 population of a gram positive or gram negative bacteria in 30 minutes, (iii-b) at least 95% of log 4 population of an enveloped virus within 30 minutes of contact of contact, (iii-c) at least 95% of a non-enveloped virus within 30 minutes of contact, and/or (iii-d) at least 94% of a log 4 population of *Clostridium difficile* bacteria within 24 hours of contact, in accordance with JIS Z 2801 (2006) test for antimicrobial activity, or a modified version of such test as described herein, (iv) a film formed from the composition has a value of 2 or less according to International Organization for Standardization (ISO) 10993-5 in vitro cytotoxicity test, (v) a durability test selected from either (v-a) a film formed from the composition kills at least 99.9% of gram-positive bacteria and gram-negative bacteria according to EPA Protocol #01-1A residual self-sanitizing activity test, or (v-b) waiting 7 days after film formation, a film formed from the composition kills at least 95% of gram-positive bacteria and gram-negative bacteria, or enveloped and non-enveloped viruses according a modified version of Protocol #01-1A residual self-sanitizing activity test, as described herein.

Test (i) refers to ASTM E1153, the entire contents of which are incorporated by reference, is a germicidal spray test (i.e., "kill now" claim) that is used to evaluate the antimicrobial efficacy of one-step cleaner-sanitizer formulations recommended for use on lightly soiled, inanimate, nonporous, non-food contact surfaces. In ASTM E1153 (last revision in 2014), the antimicrobial efficacy of sanitizers is tested on precleaned, inanimate, hard, nonporous, non-food contact surfaces against *Staphylococcus aureus, Klebsiella pneumoniae, Enterobacter aerogenes*, or a combination thereof.

Germicidal spray test results related to an inventive miscible blend formulation are set forth in Table 3 along with a comparison with three commercially available products. MS2, MRSA, and *E. coli* germicidal spray tests were conducted with two cationic polymer compositions. Composition A was a miscible blend comprising 3000 ppm non-chemically modified, linear PEI, 3000 ppm polyDADMAC, 25 ppm carboxylated branched PEI, 35% ethanol, and the balance of water. Composition B was a miscible blend comprising 200 ppm of non-chemically modified, linear PEI, 200 ppm polyDADMAC, 25 ppm branched PEI carboxylated, 70% ethanol, and the balance in water (operational pH of about 7.6).

TABLE 3

| | | | | Inventive antimicrobial compositions | |
|---|---|---|---|---|---|
| | Disinfectant only | | | A | B |
| Product name | OPTI-CIDE 3 ™ (Biotrol) | CAVICIDE1 ™ (Metrex) | ASEPTICARE ™ TB + II (Ecolab) | Time to Kill | |
| Active ingredients | Alcohol-Quat | Alcohol-Quat | Alcohol-Quat | Alcohol-Polymer charge | |
| | | Non-enveloped Virus | | | |
| MS2 (proxy for non-enveloped virus)-testing challenge 99.99% | No | No | 6 min | 2 min | 5 min |
| | | Gram Positive Bacteria | | | |
| MRSA-testing challenge 99.999% | 2 min | 1 min | 6 min | 2 min | 30 sec (with 5% soil load) |
| | | Gram Negative Bacteria | | | |
| *E. Coli*-testing challenge 99.999% | 2 min | 1 min | 6 min | 2 min | 30 sec (with 5% soil load) |

The results in Table 3 demonstrate that Composition B contained 400 ppm of cationic polymer and passed the MS2 germicidal spray test within 5 minutes of contact, which is notable since the EPA's maximum ppm standard for quaternary ammonium compounds in accordance with ASTM E1153 is 400 ppm. Moreover, the antimicrobial efficacy of some quaternary ammonium compounds is significantly diminished by soil or an organic load. As seen in Table 3, Composition B was also highly effective against MRSA and *E. Coli* spray tests (ASTM E1153) in the presence of a 5% soil load.

Test (ii) is a suspension test in accordance with ASTM E1052-96 (2002) or ASTM E2315 (2016) to determine the effectiveness of an antimicrobial solution that is in the form of a suspension against specific viruses, such as adenovirus, coronavirus, influenza viruses, rhinovirus, and rotavirus. An aliquot of the test substance is inoculated with the test virus and held for the requested exposure time. At each predetermined exposure time, an aliquot is removed, neutralized by serial dilution, and assayed for viral infectivity by an assay method specific for the test virus. Appropriate virus, test substance cytotoxicity, and neutralization controls are run concurrently. The percent and log reduction in viral infectivity are calculated as compared to the corresponding virus control. ASTM E1052-96 (2002) and ASTM E2315 (2016) are most appropriate for an antimicrobial composition that is a suspension, such as a hand sanitizer composition.

For test (iii), the ability for a film formed from the antimicrobial composition to kill gram positive and gram negative bacteria and an enveloped virus, a non-enveloped virus, and/or *Clostridium difficile* bacteria can be tested in accordance with the conditions set forth in JIS Z 2801 (2006 version, updated in 2010), which is known as the Japanese Industrial Standard Test for Antimicrobial Activity and Efficacy in Antimicrobial Products, the entire contents of which are incorporated by reference. In particular, in accordance with JIS Z 2801 (2006) or a modified version thereof, as described herein, a film formed from an antimicrobial composition of the present invention kills: (iii-a) at least 95% of log 5 population of a gram positive or gram negative bacteria in 30 minutes, (iii-b) at least 95% of log 4 population of an enveloped virus within 30 minutes of contact, (iii-c) at least 95% of a non-enveloped virus within 30 minutes of contact, and/or (iii-d) at least 94% of a log 4 population of *Clostridium difficile* bacteria within 24 hours of contact. In a preferred embodiment, a film formed from an antimicrobial composition of the present invention meets 2 or more, 3 or more, or all 4 of each of the requirements (iii-a)-(iii-d).

For example, under the conditions of this test, the JIS Z 2801 protocol demonstrated a log 4 reduction of *E. coli* on a film comprising only polyDADMAC after 30 minutes, against a log 5 challenge (Table 4).

TABLE 4

| Sample Identification | *Escherichia coli* ATCC 8739 cfu/sample | % Reduction after 30 min | Anti-microbial activity |
|---|---|---|---|
| Untreated control | $2.20 \times 10^5$ | n/a | n/a |
| 1 (pDADMAC, 12K ppm, 160 ppm titanate (LICA ™ 09), 50% EtOH, pH 3.4) | <15 | >99.99% | >4.17 |

* cfu/sample—colony forming units per sample recovered

The same film demonstrated a log 4 reduction of MRSA after 10 minutes, but with a log 7 challenge (Table 5).

TABLE 5

| Sample Identification | Methicillin Resistant *Staphylococcus aureus* ATCC 33591 cfu/sample | % Reduction after 10 min | Anti-microbial activity |
|---|---|---|---|
| Untreated control | $7.55 \times 10^6$ | n/a | n/a |
| 1 (pDADMAC, 12K ppm, 160 ppm titanate (LICA ™ 09), 50% EtOH, pH 3.4) | $7.20 \times 10^2$ | 99.99% | 4.02 |

* cfu/sample—colony forming units per sample recovered

An additional self-sanitizing ("kill later") test was devised for a residual self-sanitizing film that is believed to be more practical for a realistic utility, particularly when testing antiviral activity. This test is based on the assumption that in a real world application, an antimicrobial residual self-sanitizing film would not be covered. This test modifies JIS Z 2801 (2006 version, which was updated in 2010) by not requiring the inoculated film to be covered and starting the test time after the inoculum dries. Test results using modified JIS Z 2801 are set forth in Table 6 for determining the lysis of MS2 on a film created from a non-toxic, miscible blend of 3000 ppm non-chemically modified, linear PEI, 3000 ppm polyDADMAC, 79% ethanol, 25 ppm carboxylated branched PEI, and the balance water. The "kill later" data for gram positive and gram negative bacteria were generated using the standard JIS test.

TABLE 6

| Pathogen | % killed 1 min | % killed 5 min | % killed 10 min | % killed 15 min | % killed 20 min |
|---|---|---|---|---|---|
| Non-enveloped Virus | | | | | |
| MS2-testing 99.99% challenge | 95.00 | 99.38 | 99.96 | | |
| Gram Positive Bacteria | | | | | |
| MRSA-testing challenge 99.999% | | 99.83 | 99.99 | | |
| Gram Negative Bacteria | | | | | |
| *E. Coli*-testing challenge 99.999% | | 99.54 | | | 99.99 |

Moreover, JIS Z 2801 (2006 version, which was updated in 2010) can be modified when testing against *Clostridium difficile* bacteria by testing under lighted conditions and increasing the sample surface area from 1600 mm$^2$ to 2500 mm$^2$.

Test (iv) is directed to ISO 10993-5 (last updated in 2009), the entire contents of which are incorporated by reference, in which the in vitro cytotoxicity of medical device materials is tested. The method is directed to the incubation of cultured cells in contact with a device and/or extracts of a device either directly or through diffusion. In particular, the test article, positive and negative controls are extracted according to the method ISO 10993-12. The original extract is serially diluted and 5 concentrations are used for testing. L-929 cells (mouse, C3H/An, connective tissue) are treated with extracts of the sample, reagent control, and either negative control or positive control. Triplicate plates are prepared for each treatment. The cells are incubated for 24 hours and observed microscopically for cytotoxic effects. Cultures are observed under microscopy and graded for reactivity using a 0 to 4 scale ("4" means severely cytotoxic; "3" means moderately cytotoxic; "2" means mildly cytotoxic; "1" means slightly cytotoxic, and "0" means non-cytotoxic). Test article meets the requirement of the test when results are less than or equal to a grade of 2 (i.e., 0, 1, or 2).

A residual self-sanitizing film formed from a PEC, a miscible blend, or individual cationic polymers, as described herein, is non-leaching, and thus passes the ISO 10993-5 (2009 version) in vitro cytotoxicity test with a score of 0, as shown by the following test results in Table 7.

TABLE 7

| Sample Identification | Cytotoxic Grade | Reactivity |
|---|---|---|
| 1 (pDADMAC PEC with PAAS, 3/6 highly diluted, 6K ppm, no adhesion promoter, pH 7.2) | 0 | Non-cytotoxic |
| 2 (pDADMAC PEC with PAAS, 3/6 highly diluted, 6K ppm, 3 drops titanate (LICA ™ 09), pH 7.2) | 0 | Non-cytotoxic |
| 3 (pDADMAC PEC with PAAS, 3/6 highly diluted, 4K ppm, 3 titanate (LICA ™ 09), pH 7.2) | 0 | Non-cytotoxic |
| 4 (50% pDADMAC, 50% PEI, titanate, 4K ppm, 20% EtOH, pH 7) | 0 | Non-cytotoxic |
| 5 (linear, non-modified PEI, 4K ppm, pH 6) | 0 | Non-cytotoxic |
| Negative control | 0 | Non-cytotoxic |
| Reagent control | 0 | Non-cytotoxic |
| Positive controls | 3/4 | Moderately/severely cytotoxic |

Test (v) is directed to Protocol #01-1A, commonly known as "the Clorox test," which is a method approved by the EPA for measuring long-term sanitization claims (i.e., "kill later" durability claim). Protocol #01-1A, the entire contents of which are incorporated by reference, measures the residual self-sanitizing activity of dried chemical residues (films) on inanimate, hard, non-porous surfaces against only bacteria: *Staphylococcus aureus, Klebsiella pneumoniae,* and/or *Enterobacter aerogenes*. In particular, surfaces are inoculated, treated with test product, allowed to dry, then abraded under alternating wet and dry conditions, which are interspersed with several re-inoculations. At the end of the study and at least 24 hours later, the ability of the test surfaces to kill 99.9% of microorganisms within 5 minutes is measured. To pass this test, a film formed from the composition must maintain its antimicrobial efficacy between, and after, 12 alternating wet and dry rubs with a weighted cloth.

A modified version of the EPA's durability test, Protocol #01-1A can be used. It is believed that a modified protocol is more appropriate for evaluating residual self-sanitizing films formed from an inventive antimicrobial composition because Protocol #01-1A was designed for products that depend on killing microbes by releasing germicidal chemicals from a film and which deplete over time. The inventive antimicrobial composition does not require germicidal chemicals, but rather comprises charged, cationic polymers whose killing mechanism is not believed to deplete over time. The modified test consists of daily submitting the film to three rubs (one dry, one wet, one dry) using the EPA #01-1A protocol weight and cycle time. This modified test captures the antimicrobial effectiveness of an antimicrobial composition over days, compared to the single 24 hour measurement of the standard Protocol #01-1A. Passing the modified test will require that after 4 to 7 days, the polymer-based film will continue to demonstrate at least a 95% (e.g., at least 96%, at least 97%, at least 98%, at least 99%, at least 99.5%, at least 99.9%) reduction of gram-positive, gram-negative bacteria, enveloped virus, and/or non-enveloped virus on glass or stainless steel substrates.

The invention also provides a method of killing microbes on a surface comprising applying to the surface an antimicrobial composition comprising a cationic polymer (by itself or encapsulated in a PEC), at least one adhesion promoter (e.g., a titanate, a carboxylated branched PEI), optionally organic and/or inorganic particles that are photocatalyically active in visible light, and a carrier, each of these components are as described herein. The method can include disinfecting a surface, providing a residual self-sanitizing film, or both. The term "microbe" includes any single cell or multicellular organism, such as bacteria, viruses, fungi, archaea, and protists (e.g., algae, amoebas, protozoa). As used herein, the term "applying" refers to any suitable technique used to transfer the antimicrobial composition to a surface. For example, techniques for applying can be, but are not limited to, brushing, rolling, spraying, wiping, mopping, pouring, painting, absorbing, adsorbing, imbibing, soaking, saturating, permeating, immersing, and a combination of these methods.

Further provided is a method of killing microbes on a surface (e.g., disinfecting a surface, providing a residual self-sanitizing film, or both) comprising applying to the surface an antimicrobial composition comprising a high molecular weight (preferably an ultra-high molecular weight) polydiallyldimethylammonium salt (e.g., polydiallyldimethylammonium halide) and a carrier, as described herein. The antimicrobial composition of this embodiment can further comprise (i) a polyethylenimine-based polymer, chitosan, or a combination thereof, and/or (ii) an anionic polymer, and/or (iii) organic and/or inorganic particles that are photocatalyically active in visible light, and/or (iv) at least one adhesion promoter (e.g., a titanate, a carboxylated branched PEI), and/or (v) at least one salt. Each of these optional components is as described herein.

Once applied to the surface, the carrier, as described herein, in the composition evaporates to leave an antimicrobial residual self-sanitizing film on the surface. The antimicrobial residual self-sanitizing film renders the surface bactericidal, virucidal, and/or germicidal. As used herein, the term "renders the surface bactericidal, virucidal, and/or germicidal" refers to reducing (e.g., eliminating, killing, or preventing and/or inhibiting growth) the presence of bacteria, viruses, and/or germs (including a fungus, such as *Aspergillas brasliensis*) to any suitable degree. As used herein, the term "any suitable degree" refers to 50% reduction or more, including 60% reduction or more, 70% reduction or more, 80% reduction or more, 90% reduction or more, 92% reduction or more, 94% reduction or more, 95% reduction or more, 97% reduction or more, 98% reduction or more, 99% reduction or more, or 99.5% elimination or more.

In accordance with this embodiment, the invention provides a coated surface comprising a surface (e.g., a surface of a substrate) and an antimicrobial residual self-sanitizing film, as described herein, that is applied to the surface. The resulting film provides a non-leaching surface that is not easily removed. In most embodiments, the antimicrobial residual self-sanitizing film is not covalently bound to the surface (e.g., surface of the substrate).

The surface that is rendered bactericidal, virucidal, and/or germicidal can be of any suitable material, including a biocompatible material. The surface can be used in or derived from any suitable form, such as, for example, a powder, dust, an aggregate, an amorphous solid, a sheet, a fiber, a tube, a fabric, or the like. In embodiments, the surface comprises metal, glass, fiberglass, silica, sand, wood, fiber, natural polymer, synthetic polymer, plastic, rubber, ceramic, porcelain, stone, marble, cement, a human or animal body (e.g., skin), or any hybrid, alloy, copolymer, blend, or combination thereof.

Metal surfaces suitable for use in the invention include, for example, stainless steel, nickel, titanium, tantalum, aluminum, copper, gold, silver, platinum, zinc, nickel titanium alloy (nitinol), an alloy of nickel, chromium, and iron (INCONEL™, Special Metals, Corporation, Elkhart, Ind.), iridium, tungsten, silicon, magnesium, tin, galvanized steel, hot dipped galvanized steel, electrogalvanized steel, annealed hot dipped galvanized steel, alloys of any of the foregoing metals, coatings containing any of the foregoing metals, and combinations thereof.

Glass surfaces suitable for use in the invention include, for example, soda lime glass, strontium glass, borosilicate glass, barium glass, glass-ceramics containing lanthanum, fiber glass, and combinations thereof.

Silica surfaces suitable for use in the invention include, for example, quartz, fused quartz, crystalline silica, fumed silica, silica gel, silica aerogel, and mixtures thereof.

Sand surfaces suitable for use in the invention include, for example, sand comprised of silica (e.g., quartz), calcium carbonate (e.g., aragonite), and mixtures thereof. The sand can comprise other components, such as minerals (e.g., magnetite, chlorite, glauconite, gypsum, olivine, garnet), metal (e.g., iron), shells, coral, limestone, and/or rock.

Suitable wood surfaces include, for example, hard wood and soft wood, and materials engineered from wood, wood chips, or fiber (e.g., plywood, oriented strand board, laminated veneer lumber, composites, strand lumber, chipboard, hardboard, medium density fiberboard), and combinations thereof. Types of wood include alder, birch, elm, maple, willow, walnut, cherry, oak, hickory, poplar, pine, fir, and combinations thereof.

Fiber surfaces suitable for use in the invention include, for example, natural fibers (e.g., derived from an animal, vegetable, or mineral) and synthetic fibers (e.g., derived from cellulose, mineral, or polymer). Suitable natural fibers include cotton, hemp, jute, flax, ramie, sisal, bagasse, wood fiber, silkworm silk, spider silk, sinew, catgut, wool, sea silk, wool, mohair, angora, and asbestos. Suitable synthetic fibers include rayon (e.g., lyocell), modal, and metal fiber (e.g., copper, gold, silver, nickel, aluminum, iron), carbon fiber, silicon carbide fiber, bamboo fiber, seacell, nylon, polyester, polyvinyl chloride fiber (e.g., vinyon), polyolefin fiber (e.g., polyethylene, polypropylene), acrylic polyester fiber, aramid (e.g., TWARON™, KEVLAR™, or NOMEX™), spandex, and combinations thereof.

Natural polymer surfaces suitable for use in the invention include, for example, a polysaccharide (e.g., cotton, cellulose), shellac, amber, wool, silk, natural rubber, a biopolymer (e.g., a protein, an extracellular matrix component, collagen), and combinations thereof.

Synthetic polymer surfaces suitable for use in the invention include, for example, polyvinylpyrrolidone, acrylics, acrylonitrile-butadiene-styrene, polyacrylonitrile, acetals, polyphenylene oxides, polyimides, polystyrene, polypropylene, polyethylene, polytetrafluoroethylene, polyvinylidene fluoride, polyvinyl chloride, polyethylenimine, polyesters, polyethers, polyamide, polyorthoester, polyanhydride, polysulfone, polyether sulfone, polycaprolactone, polyhydroxybutyrate valerate, polylactones, polyurethanes, polycarbonates, polyethylene terephthalate, as well as copolymers and combinations thereof.

Typical rubber surfaces suitable for use in the invention include, for example, silicones, fluorosilicones, nitrile rubbers, silicone rubbers, polyisoprenes, sulfur-cured rubbers, butadiene-acrylonitrile rubbers, isoprene-acrylonitrile rubbers, and combinations thereof.

Ceramic surfaces suitable for use in the invention include, for example, boron nitrides, silicon nitrides, aluminas, silicas, combinations thereof, and combinations thereof.

Stone surfaces suitable for use in the invention include, for example, bauxite, calcite, feldspar, gypsum, slate, granite, quartz, quartzite, limestone, dolostone, sandstone, marble, soapstone, serpentine and combinations thereof.

For purposes of the present invention, animal bodies include, but are not limited to, the order Rodentia (e.g., mice), the order Logomorpha (e.g., rabbits), the order Carnivora (e.g., Felines (cats) and Canines (dogs)), the order Artiodactyla (e.g., Bovines (cows) and Swines (pigs)), the order Perssodactyla (e.g., Equines (horses)), the order Primates, Ceboids, or Simioids (e.g., monkeys), the class Ayes (e.g., birds), the class of Phylum Arthropoda (e.g., insects), the class of Pisces (e.g., fish), or the order Anthropoids (e.g., humans and apes). Typically skin (including intact skin, wounded or broken skin, and/or skin that is otherwise damaged, by for example, a burn) and/or mucosal tissue (e.g., oral, nasal, ocular, or genital tissue) of the animal body serves as the surface suitable for application of the antimicrobial composition. The skin and/or mucosal tissue can be associated with any part of the animal body, including the limbs, tail, abdomen, chest, head, neck, face, genital area (e.g., udder), buttocks, or back. In general, the type and amount of components of the antimicrobial composition will be selected to ensure biocompatibility, to minimize toxicity, to minimize irritation, and/or have a desired level of surface tack and/or adhesiveness of the formed film.

The surface typically is a component of a larger structure. For example, the surface can be part of a substrate, such as a medical device, diagnostic equipment, implant, glove, mask, curtain, mattress, sheets, blankets, gauze, dressing, tissue, surgical drape, tubing, surgical instrument, safety gear, fabric, apparel item, floor, handles, wall, sink, shower or tub, toilet, furniture, wall switch, toy, athletic equipment, playground equipment, shopping cart, countertop, appliance, railing, door, air filter, pipe, utensil, dish, cup, container, object display container, food, food display container, food package, food processing equipment, food handling equipment, food transportation equipment, food vending equipment, food storage equipment, food packaging equipment, plant, phone, cell phone, remote control, computer, mouse, keyboard, touch screen, leather, cosmetic, cosmetic making equipment, cosmetics storage equipment, cosmetics packaging equipment, personal care item, personal care item making equipment, personal care storage equipment, personal care packaging equipment, animal care item, animal care item making equipment, veterinary equipment, powder, cream, gel, salve, eye care item, eye care item making equipment, contact lens, glasses, eye care storage equipment, contact lens case, jewelry, jewelry making equipment, jewelry storage equipment, animal housing, farming equipment, animal food handling equipment, animal food storage space, animal food storage equipment, animal food container, air vehicle, land vehicle, air processing equipment, air filter, water vehicle, water storage space, water storage equipment, water processing equipment, water storage container, water filter, hand, hair, foot, leg, arm, torso, head, or animal body part, pharmaceuticals display container, pharmaceuticals package, pharmaceuticals processing equipment, pharmaceuticals handling equipment, pharmaceuticals transportation equipment, pharmaceuticals vending equipment, pharmaceuticals, pharmaceuticals storage equipment, pharmaceuticals packaging equipment.

A "medical device" includes any device having surfaces that contact tissue, blood, or other bodily fluids in the course of their use or operation, which are found on or are subsequently used within a mammal (e.g., a human) Medical devices include, for example, extracorporeal devices for use in surgery, such as blood oxygenators, blood pumps, blood storage bags, blood collection tubes, blood filters including filtration media, dialysis membranes, tubing used to carry blood and the like which contact blood which is then returned to the patient or mammal. Medical devices also include endoprostheses implanted in a mammal (e.g., a human), such as vascular grafts, stents, pacemaker leads, surgical prosthetic conduits, heart valves, and the like, that are implanted in blood vessels or the heart. Medical devices also include devices for temporary intravascular use such as catheters, guide wires, amniocentesis and biopsy needles, cannulae, drainage tubes, shunts, sensors, transducers, probes and the like which are placed into the blood vessels, the heart, organs or tissues for purposes of monitoring or repair or treatment. Medical devices also include prostheses such as artificial joints such as hips or knees as well as artificial hearts. In addition, medical devices include penile implants, condoms, tampons, sanitary napkins, ocular lenses, sling materials, sutures, hemostats used in surgery, antimicrobial materials, surgical mesh, transdermal patches, and wound dressings/bandages.

The "diagnostic equipment" includes any device or tool used to diagnose or monitor a medical condition. Examples include an ultrasound, magnetic resonance imaging (MRI) machine, positron emission tomography (PET) scanner, computed tomography (CT) scanner, ventilator, heart-lung machine, extracorporeal membrane oxygenation (ECMO) machine, dialysis machine, blood pressure monitor, otoscope, ophthalmoscope, stethoscope, sphygmomanometer, blood pressure cuff, electrocardiograph, thermometer, defibrillator, speculum, sigmoidoscope, and anoscope.

The "surgical instrument" includes any tool or device used for performing surgery or an operation. Examples include a scalpel, lancet, trocar, hemostat, grasper, forceps, clamp, retactor, distractor, positioner, tracheotome, dilator, stapler, irrigation needle, injection needle, drill, scope, endoscope, probe, ruler, and caliper.

"Safety gear" includes devices used to protect a person, animal, or object. Examples of "safety gear" are a mask, face shield, visor, goggles, glasses, gloves, shoe covers, foot guard, leg guard, belt, smock, apron, coat, vest, raingear, hat, helmet, chin strap, hairnet, shower cap, hearing protection (ear plugs, ear muffins, hearing bands), respirator, gas mask, supplied air hood, collar, leash, and first aid kit.

"Fabric" includes any type of suitable fabric, such as bedding, curtains, towels, table coverings, protective sheeting, and dish cloths.

An "apparel item" includes an item of clothing, footwear, or other item someone would wear on his/her person. Examples include a uniform, coat, shirt, pants, waders, scrubs, socks, shoe or boot liner, an insole, gloves, hats, shoes, boots, and sandals.

The surface can be part of a building structure or an item that can be found in a building structure, such as a floor, wall, an appliance (e.g., a refrigerator, oven, stove, dishwasher, washing machine, clothes dryer, furnace, water heater, air conditioner, heater), sink, shower or tub, toilet, furniture (e.g., mattress, couch, sofa, chair, table, shelf, mantle, bed, dresser), countertop, railing, air filter, air processing equipment, water processing equipment, water filter, pipe, door, handle, light, light switch, thermostat, sprinkler, air conditioner evaporator and/or condenser.

The surface can also be a toy or athletic equipment, including exercise equipment, playground equipment, or a pool.

The surface can be a utensil (e.g., knife, fork, spoon, ladle, spatula, whisk, etc.), a dish (e.g., a food storage container, a food serving piece, etc.), a food package (e.g., a bag, a box, foil, plastic wrap), or other item that comes in contact with food (e.g., a cutting board, food display container, food processing equipment, food handling equipment, food transportation equipment, food vending equipment, animal food handling equipment, animal food storage space, food storage equipment, animal food container, animal food storage equipment). The surface can be part of food processing equipment, such as food processing tanks, stirrers, conveyor belts, knives, grinders, packaging machines, labeling machines, etc.

The "food" is any food in which it would be desirable to provide with an antimicrobial residual self-sanitizing film. In such embodiments, the antimicrobial residual self-sanitizing film and the composition thereof should be nontoxic for human and animal consumption. The "food" can be, e.g., any fruit, vegetable, meat, or egg.

The "plant" is any suitable plant, including an angiosperm (a flowering plant), gymnosperm (a seed-producing plant), a conifer, fern, and moss. Suitable angiosperms are from the *amborella* (e.g., *Amborella trichopoda Baill*), nymphaeales (e.g., water lily), austrobaileyales (e.g., *Illicium verum*), chloranthales (e.g., from the genus ascarina, chloranthus, hedyosmum, or sarcandra), magnoliids (e.g., *magnolia*, bay laurel, black pepper), monocots (e.g., grasses, orchids, palms), ceratophyllum (e.g., aquatic plants), or eudicots (e.g., sunflower, *petunia*, apple) groups. Suitable gymnosperms are from the subclass cycadidae, ginkgoidae, gnetidae, or pinidae.

The surface can be part of an electronic device, such as a phone, cell phone, remote control, computer, mouse, keyboard, and touch screen.

The surface can further be part of a cosmetic (e.g., eye shadow, eyeliner, primer, foundation, lipstick, lip gloss, blush), cosmetic making equipment, cosmetic storage equipment, cosmetic packaging equipment, a personal care item (e.g., cream, gel, salve, lip balm, body soap, facial soap, lotion, cologne, perfume, antiperspirant, deodorant, facial tissue, cotton swabs, cotton pads, mouthwash, toothpaste, nail polish, shampoo, conditioner, hairspray, talcum powder, shaving cream, contact lens, contact lens case, glasses), personal care item making equipment, personal care storage equipment, personal care packaging equipment, jewelry (e.g., necklace, ring, earring, bracelet, watch), jewelry making equipment, or jewelry storage equipment.

The "animal care item" and "veterinary equipment" can be any product used in a setting that includes animals, such as a house, boarding house, or veterinary hospital. Of course, veterinary equipment can be used at a location outside of a hospital setting. Animals are any animals that are typically considered pets, non-pets, boarded, treated by a veterinarian, and animals in the wild. Examples include a dog, cat, reptile, bird, rabbit, ferret, guinea pig, hamster, rat, mouse, fish, turtle, horse, goat, cattle, and pigs. Suitable animal care items include the personal care items described herein, toys, bed, crate, kennel, carrier, bowl, dish, leash, collar, litterbox, and grooming items (e.g., clippers, scissors, a brush, comb, dematting tool, and deshedding tool). Suitable veterinary equipment includes any of the medical devices and surgical instruments described herein and other equipment, such as a table, tub, stretcher, sink, scale, cage, carrier, and leash.

The "animal housing" can be any suitable housing, such as a coop, stable, shelter, grab bag shelter, hutch, barn, shed, pen, nestbox, feeder, stanchion, cage, carrier, or bed.

The "farming equipment" is any device used in an agricultural setting, including a farm or ranch, particularly a farm or ranch that houses animals, processes animals, or both. Animal livestock that can be housed or processed as described herein and include, e.g., horses, cattle, bison, and small animals such as poultry (e.g., chickens, quails, turkeys, geese, ducks, pigeons, doves, pheasants, swan, ostrich, guineafowl, Indian peafowl, emu), pigs, sheep, goats, alpacas, llamas, deer, donkeys, rabbits, and fish. Examples of farming equipment include as a wagon, trailer, cart, barn, shed, fencing, sprinkler, shovel, scraper, halter, rope, restraining equipment, feeder, waterer, trough, water filter, water processing equipment, stock tank, fountain, bucket, pail, hay rack, scale, poultry flooring, egg handling equipment, a barn curtain, tractor, seeder, planter, plow, rotator, tiller, spreader, sprayer, agitator, sorter, baler, harvester, cotton picker, thresher, mower, backhoe loader, squeeze chute, hydraulic chute, head chute, head gate, crowding tub, corral tub, alley, calving pen, calf table, and milking machine.

The surface can be part of a vehicle, such as an air vehicle, land vehicle, or water vehicle. Suitable vehicles include a car, van, truck, bus, ambulance, recreational vehicle, camper, motorcycle, scooter, bicycle, wheelchair, train, streetcar, ship, boat, canoe, submarine, an unmanned underwater vehicle (UUV), a personal water craft, airplane, jet, helicopter, unmanned autonomous vehicle (UAV), and hot air balloon.

If desired, the surface to which the antimicrobial residual self-sanitizing film has been applied can be regenerated by removing the antimicrobial residual self-sanitizing film, since the film typically is not covalently bonded to the surface. The removing step can be performed by any suitable method, such as washing or rinsing with a solvent (e.g., water and/or alcohol). Thus, the antimicrobial coating on a surface (e.g., the surface of a substrate) described herein can be considered temporary (e.g., removable). In an embodiment, the antimicrobial residual self-sanitizing film is water soluble and is removable with water (e.g., hot soapy water).

The antimicrobial residual self-sanitizing film renders the surface bactericidal against any suitable bacteria to any suitable degree. In other words, an antimicrobial composition of the present invention can form an antimicrobial residual self-sanitizing film on a surface (e.g., the surface of a substrate) that kills at least 75% (e.g., at least 80%, at least 85%, at least 90%, at least 92%, at least 94%, at least 95%, at least 96%, at least 97%, at least 98%, at least 99%, or at least 99.5%) of bacteria that comes in contact with the antimicrobial residual self-sanitizing film. For example, the bacteria can be, for example, *Staphylococcus aureus*, gram positive methicillin-resistant *Staphylococcus aureus* (MRSA), *Staphylococcus saprophyticus*, *Pseudomonas aeruginosa*, *Listeria monocytogenes*, *Klebsiella pneumoniae*, *Streptococcus pneumoniae*, *Streptococcus pyogenes*, *Streptococcus agalactiae*, *Haemophilus influenzae*, *Helicobacter pylori*, *Salmonella*, *Shigella*, *Clostridium*, *Enterobacter aerogenes*, gram negative *Escherichia coli*, *Clostridium difficile*, or a combination thereof. In certain embodiments, the antimicrobial composition is effective in reducing (e.g., eliminating, killing, or preventing and/or inhibiting growth) gram positive methicillin-resistant *Staphylococcus aureus* (MRSA), gram negative *Escherichia coli* (ATCC 8739), *Clostridium difficile* (ATCC 43598), or a combination thereof.

In an aspect of the invention, an antimicrobial residual self-sanitizing film formed from an antimicrobial composition described herein renders the surface bactericidal against gram positive methicillin-resistant *Staphylococcus aureus* (MRSA) bacteria. Preferably, the antimicrobial residual self-sanitizing film kills at least 95% (e.g., at least 96%, at least 97%, at least 98%, at least 99%) of a log 5 population of gram positive methicillin-resistant *Staphylococcus aureus* (MRSA) bacteria within 30 minutes (e.g., within 20 minutes, within 15 minutes, within 10 minutes, within 5 minutes) of contact. In a particularly preferred embodiment, the antimicrobial residual self-sanitizing film kills at least 99.8% of a log 5 population of gram positive methicillin-resistant *Staphylococcus aureus* (MRSA) bacteria within 5 minutes of contact.

In another aspect of the invention, an antimicrobial residual self-sanitizing film formed from an antimicrobial composition described herein renders the surface bactericidal against gram negative *Escherichia coli* (ATCC 8739) bacteria. In particular, the antimicrobial residual self-sanitizing film kills at least 95% (e.g., at least 96%, at least 97%, at least 98%, at least 99%) of a log 5 population of gram negative *Escherichia coli* (ATCC 8739) bacteria within 30 minutes (e.g., within 20 minutes, within 15 minutes, within 10 minutes, within 5 minutes) of contact. In a preferred embodiment, the antimicrobial residual self-sanitizing film kills at least 99.7% of a log 5 population of gram negative *Escherichia coli* (ATCC 8739) bacteria within 5 minutes of contact.

In yet another aspect of the invention, an antimicrobial residual self-sanitizing film formed from an antimicrobial composition described herein renders the surface bactericidal against *Clostridium difficile* (ATCC 43598) bacteria. More specifically, the antimicrobial residual self-sanitizing film kills at least 75% (e.g., at least 80%, at least 85%, at least 90%, at least 95%, at least 97%, at least 98%, at least 99%) of a log 4 population of *Clostridium difficile* (ATCC 43598) bacteria within 24 hours of contact (e.g., within 18 hours, within 12 hours, within 10 hours, within 8 hours, within 6 hours) of contact. In a preferred embodiment, the antimicrobial residual self-sanitizing film kills at least 99.7% of a log 4 population of *Clostridium difficile* (ATCC 43598) bacteria within 8 hours of contact.

Viruses are much more difficult to kill, especially non-enveloped viruses, e.g., norovirus, rotavirus, adenovirus, and poliovirus. Generally, the only way to kill an array of non-enveloped viruses is with an abundance of very harsh chemicals such as hypochlorite, acids and peroxides, all of which are extremely cytotoxic. Remarkably, the technology described in the present invention is capable of forming antimicrobial residual self-sanitizing films that kill non-enveloped viruses. Accordingly the present invention provides an antimicrobial residual self-sanitizing film formed from an antimicrobial composition described herein that renders a surface virucidal against any suitable virus to any suitable degree, such as, reducing (e.g., eliminating, killing, or preventing and/or inhibiting growth) at least 75% (e.g., at least 80%, at least 85%, at least 90%, at least 92%, at least 94%, at least 95%, at least 96%, at least 97%, at least 98%, at least 99%, or at least 99.5%) of the virus. In a particular example, an antimicrobial residual self-sanitizing film formed from an antimicrobial composition described herein renders the surface virucidal against at least one enveloped virus (e.g., chickenpox virus, influenza, herpes simplex, severe acute respiratory syndrome (SARS), flavivirus, togavirus) or non-enveloped virus (e.g., levivirus, norovirus, rotavirus, adenovirus, parvovirus, and poliovirus).

In another aspect of the invention, an antimicrobial residual self-sanitizing film formed from an antimicrobial composition described herein renders the surface virucidal against influenza A (e.g., H1N1, H1N2, and H5N1) enveloped virus. In an embodiment, the antimicrobial residual self-sanitizing film kills at least 95% (e.g., at least 96%, at least 97%, at least 98%, at least 99%) of a log 4 population of influenza A (H1N1) (ATCC CCL-34) enveloped virus within 60 minutes (e.g., within 45 minutes, within 30 minutes, within 20 minutes) of contact. In a preferred embodiment, the antimicrobial residual self-sanitizing film kills at least 99% of a log 4 population of influenza A (H1N1) (ATCC CCL-34) enveloped virus within 30 minutes of contact of contact.

In yet another aspect of the invention, an antimicrobial residual self-sanitizing film renders the surface virucidal against a non-enveloped virus, such as levivirus (e.g., MS2), norovirus, rotavirus, adenovirus, parvovirus, or poliovirus. In an embodiment, the antimicrobial residual self-sanitizing film kills at least 95% (e.g., at least 96%, at least 97%, at least 98%, at least 99%) of a non-enveloped virus within 30 minutes of contact (e.g., within 20 minutes, within 15 minutes, within 10 minutes, within 5 minutes) of contact. In a preferred embodiment, the antimicrobial residual self-sanitizing film kills at least 97% of a non-enveloped virus within 5 minutes of contact. In some instances of this embodiment, the non-enveloped virus is MS2 (ATCC 15597-B1).

One embodiment of the invention is directed to treated filter media that comprises one or more insoluble cationic polymers, as described herein, that is coupled to positively charged non-woven filter media. The filter media is suitable for filtering, for example, liquids (e.g., water) and air and can be made from any suitable material, such as alumina ($Al_2O_3$), polyester (e.g., PET), polyethylene, polypropylene, polyamide (e.g., nylon 6,6), polyimide, polyacrylic, glass, metal, dextran, cellulose, jute, wood pulp, cotton, or a combination thereof (e.g., microglass fibers and/or cellulose coated with nanoalumina fibers). If the material is not positively charged in its natural form, the material can be modified, as needed, to provide the necessary positive charge, by for example, adding one or more quaternary ammonium groups. The non-woven filter media can be purchased commercially and can be prepared by any suitable method (e.g., wetlaid, airlaid, drylaid, meltblown, spunbond, nanofiber web spinning, and continuous draw fiberization). See, e.g., Argonide (Sanford, Fla.), Pall Corporation (Port Washington, N.Y.), GE Infrastructure Water and Process Technologies (Trevose, Pa.), and Meissner Filtration Products (Camarillo, Calif.). An adhesion promoter that acts as a coupling agent, as described herein, can be used. Embodiments in which the adhesion promoter is cationic, such as branched carboxolated PEI, are preferred.

Figure 2A:
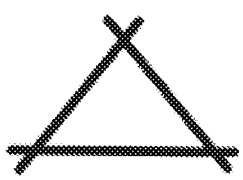
FIG. 2A illustrates a small pore size from a filter comprising 5 μm glass that is not positively charged.
Figure 2B:
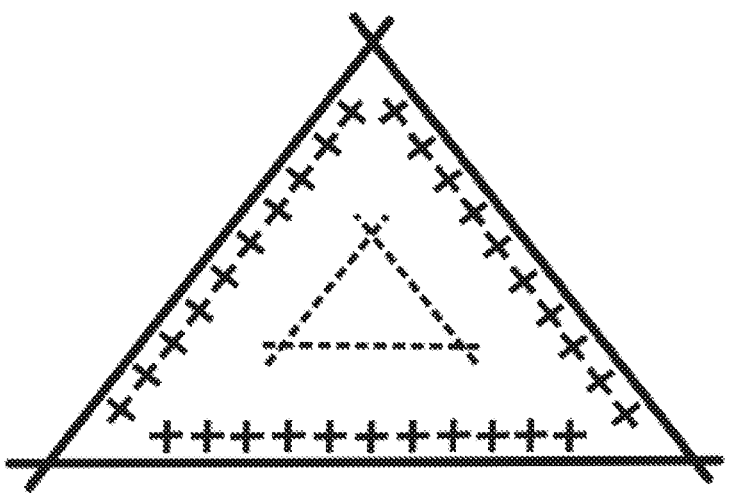
FIG. 2B illustrates a filter comprising positively charged alumina with a larger pore size and a cationic polymer coupled to the alumina.

Most filtration media reduce pathogenic microbes by simple screening by size, but such filters require high pressure to effective screen a material (e.g., fluid), easily foul, and require frequent maintenance. A treated filter that is positively charged and coupled to one or more insoluble cationic polymers, as described herein, can effectively kill microorganisms with reduced pressure and/or less fouling. FIG. 2A illustrates a small pore size from a filter comprising 5 µm glass that is not positively charged. FIG. 2B illustrates a filter comprising positively charged alumina with a larger pore size. However, the filter acts like the smaller pore sized microglass filter in FIG. 2A, because of the cationic polymer (e.g., insoluble polyDADMAC, linear PEI) that is coupled to the alumina.

In one example of a treated water filter, polyDADMAC that has been made insoluble (e.g., by substituting part of the chloride counterions with fluoride) is coupled to positively charged, non-woven filter $Al_2O_3$ media with branched carboxylated PEI. The resulting treated filter media has a very high positive zeta value. In another example, a treated air filter is made by coupling linear PEI to positively charged, non-woven filter $Al_2O_3$ media using an adhesion promoter, such as branched carboxylated PEI.

Upon testing, a highly contaminated (log 7) metal working fluid passed through a treated filter, as described herein, reduced microbes, including a non-enveloped virus, by 99.9%.

The invention is further illustrated by the following embodiments.

(1) An antimicrobial composition comprising: (a) a cationic polymer, (b) at least one adhesion promoter, (c) optionally organic and/or inorganic particles that are photocatalytically active in visible light, and (d) a carrier, wherein the components of the composition are not covalently bound to one another, and the antimicrobial composition is in accordance with one or more of the following tests: (i) a germicidal spray test according to American Society for Testing and Materials (ASTM) international method E1153 that meets the EPA requirement of log 3 reduction for viruses and a log 5 reduction for bacteria, (ii) a suspension test according to ASTM international method E1052-96 (2002) or ASTM international method E2315 (2016), (iii) a film formed from the composition kills (iii-a) at least 95% of log 5 population of a gram positive or gram negative bacteria in 30 minutes, (iii-b) at least 95% of log 4 population of an enveloped virus within 30 minutes of contact of contact, (iii-c) at least 95% of a non-enveloped virus within 30 minutes of contact, (iii-d) at least 94% of a log 4 population of *Clostridium difficile* bacteria within 24 hours of contact, in accordance with Japanese Industrial Standard (JIS) Z 2801 (2006) test for antimicrobial activity, or a modified version of such test as described herein, (iv) a film formed from the composition has a value of 2 or less according to International Organization for Standardization (ISO) 10993-5 in vitro cytotoxicity test; and (v) a durability test selected from either (v-a) a film formed from the composition kills at least 99.9% of gram-positive bacteria and gram-negative bacteria according to Environmental Protection Agency (EPA) Protocol #01-1A residual self-sanitizing activity test, or (v-b) waiting 7 days after film formation, a film formed from the composition kills at least 95% of gram-positive bacteria and gram-negative bacteria, or enveloped and non-enveloped viruses according a modified version of Protocol #01-1A residual self-sanitizing activity test, as described herein.

(2) The antimicrobial composition of embodiment (1), wherein the cationic polymer is a polydiallyldialkylammonium salt, an acryloxyalkyltrialkylammonium salt, a vinylphenalkyltrialkylammonium salt, an acrylamidoalkyltrialkylammonium salt, a poly(acrylamide-co-diallyldialkylammonium salt), a polyethylenimine-based polymer, chitosan optionally used in combination with an anionic polymer, or a combination thereof.

(3) The antimicrobial composition of embodiment (2), wherein the polydiallyldialkylammonium salt is a polydiallyldimethylammonium halide, and the halide is chloride, fluoride, an anion containing chloride, an anion containing fluoride, or a combination thereof.

(4) The antimicrobial composition of any one of embodiments (1)-(3), wherein the cationic polymer is non-chemically modified linear polyethylenimine (PEI).

(5) The antimicrobial composition of any one of embodiments (1)-(4), wherein the at least one adhesion promoter is selected from a titanate, carboxylated branched or linear PEI, a silane compound, cationic block copolymers, and a polymer comprising at least one acyl group, carboxylic acid group, or carboxylic acid derivative, and a combination thereof.

(6) The antimicrobial composition of any one of embodiments (1)-(5), wherein the organic and/or inorganic particles that are photocatalytically active in visible light are selected from the group consisting of graphene, g-$C_3N_4$, a transition metal oxide, a transition metal sulfide, a transition metal selenide, a dye sensitizer, a conjugated polymer, a noble metal, or a mixture thereof.

(7) The antimicrobial composition of any one of embodiments (1)-(6), wherein the organic and/or inorganic particles that are photocatalytically active in visible light are W- and N-doped $TiO_2$ particles that have been hydrolyzed under ultraviolet (UV) light.

(8) The antimicrobial composition of any one of embodiments (1)-(7), wherein the antimicrobial composition does not contain a germicidal small molecule compound.

(9) The antimicrobial composition of any one of embodiments (1)-(7), wherein the antimicrobial composition further comprises at least one germicidal agent.

(10) The antimicrobial composition of any one of embodiments (1)-(9), wherein the antimicrobial composition further comprises one or more non-electrolyte polymers.

(11) The antimicrobial composition of embodiment (10), wherein the one or more non-electrolyte polymers comprises a polyacrylamide.

(12) A method of killing microbes on a surface comprising applying to the surface the antimicrobial composition of any one of embodiments (1)-(11).

(13) The method of embodiment (12), wherein the carrier evaporates to leave a residual self-sanitizing film on the surface.

(14) The method of embodiment (13), wherein the residual self-sanitizing film renders the surface bactericidal, virucidal, and/or germicidal.

(15) The method of embodiment (13) or (14), wherein the residual self-sanitizing film kills one or more of the following: (i) at least 95% of a log 5 population of gram positive methicillin-resistant *Staphylococcus aureus* (MRSA) bacteria within 30 minutes of contact; (ii) at least 95% of a log 5 population of gram negative *Escherichia coli* (ATCC 8739) bacteria within 30 minutes of contact; (iii) at least 95% of a log 4 population of influenza A (H1N1) (ATCC CCL-34) enveloped virus within 60 minutes of contact; (iv) at least 95% of a non-enveloped virus within 30 minutes of contact of contact; and/or (v) at least 75% of a log 4 population of *Clostridium difficile* (ATCC 43598) bacteria within 24 hours of contact of contact.

(16) The method of embodiment (15), wherein the non-enveloped virus is MS2 (ATCC 15597-B1).

(17) An antimicrobial composition comprising a polyethylenimine-based polymer, optionally a second cationic polymer selected from a polydiallyldialkylammonium salt, a poly(acrylamide-co-diallyldialkylammonium halide), chitosan, or a combination thereof, optionally a polyacid, optionally at least one adhesion promoter, and a carrier.

(18) The antimicrobial composition of embodiment (17), wherein the polyethylenimine-based polymer is linear PEI.

(19) The antimicrobial composition of embodiment (17) or (18), wherein the composition comprises non-chemically modified linear PEI, polydiallyldimethylammonium chloride (polyDADMAC), optionally citric acid, a carboxylated branched PEI, and a water-alcohol carrier.

(20) The antimicrobial composition of any one of embodiments (17)-(19), wherein the composition comprises citric acid.

(21) A method of killing microbes on a surface comprising applying to the surface the antimicrobial composition of any one of embodiments (17)-(20).

(22) An antimicrobial composition comprising at least one organic and/or inorganic particle that is photocatalytically active in visible light, at least one adhesion promoter, and a carrier, wherein a film formed from the antimicrobial composition kill microbes under the conditions of JIS Z 2801 that has been modified by not requiring the inoculated film to be covered and starting the test time after the inoculum dries.

(23) A method of killing microbes on a surface comprising applying to the surface the antimicrobial composition of embodiment (22).

(24) A method of killing microbes on a surface comprising applying to the surface an antimicrobial composition comprising high molecular weight polydiallyldialkylammonium salt and a carrier.

(25) The method of embodiment (24), wherein the antimicrobial composition further comprises a polyethylenimine-based polymer, chitosan, or a combination thereof.

(26) The method of embodiment (24) or (25), wherein the antimicrobial composition further comprises organic and/or inorganic particles that are photocatalytically active in visible light.

(27) The method of any one of embodiments (24)-(26), wherein the antimicrobial composition does not contain a germicidal small molecule compound.

(28) The method of any one of embodiments (24)-(27), wherein the carrier evaporates to leave a residual self-sanitizing film on the surface.

(29) The method of embodiment (28), wherein the residual self-sanitizing film kills one or more of the following: (i) at least 95% of a log 5 population of gram positive methicillin-resistant *Staphylococcus aureus* (MRSA) bacteria within 30 minutes of contact; (ii) at least 95% of a log 5 population of gram negative *Escherichia coli* (ATCC 8739) bacteria within 30 minutes of contact; (iii) at least 95% of a log 4 population of influenza A (H1N1) (ATCC CCL-34) enveloped virus within 60 minutes of contact; (iv) at least 95% of a non-enveloped virus within 30 minutes of contact of contact; and/or (v) at least 75% of a log 4 population of *Clostridium difficile* (ATCC 43598) bacteria within 24 hours of contact of contact.

The following examples further illustrate the invention but, of course, should not be construed as in any way limiting its scope.

EXAMPLES

The antimicrobial compositions for the following examples were prepared according to the following general procedure: (1) a highly dilute mixture of one or more cationic polymers is prepared, (2) photocatalyst particles are added as a percent weight based on cationic monomers (% wbcm), (3) a highly dilute mixture of one or more anionic polymers is prepared, (4) the dilute cationic polymer and the dilute anionic polymers are blended to create a PEC, (5) if used, a titanate adhesion promoter is added as a percent weight based on total monomers (% wbtm), (6) the cationic/anionic PEC is condensed (i.e., the solvent is partially evaporated) to obtain the desired concentration used in determining, for example, film thickness and film durability, and (7) the antimicrobial composition is further diluted for desired modifications. Steps 2-7 are optional depending on the desired disinfecting composition and concentration.

Example 1

This example demonstrates the preparation of an antimicrobial composition in an embodiment of the invention.

The individual components and their relative amounts for forming a polyDADMAC/PEI/PAAS PEC are tabulated and provided in Table 8. The amounts of the individual components are listed in addition to a calculation of the concentration (ppm) of the solution.

TABLE 8

| Components | Mass (g) | % Solids | Solids (g) | $H_2O$ (g) | Cationic Solids in $H_2O$ (g) | Anionic Solids in $H_2O$ (g) | % of total fluid | Charged monomer Ratio of $n^-/n+$ |
|---|---|---|---|---|---|---|---|---|
| pDADMAC | 3 | 40% | 1.2 | 775.4 | 1.2 | | 0.21% | 0.25 |
| PEI | 0.6 | 100% | 0.6 | 100 | 0.6 | | 0.05% | |
| PAAS | 1.5 | 30% | 0.45 | 293.85 | | 0.45 | | |
| g $H_2O$ for pDADMAC mix | 773.6 | | | Total Cationic Polymer | 1.8 | 0.45 | Total Anionic Polymer | |
| g $H_2O$ in bulk pDADMAC | 1.8 | Titanate (% wbtm) | | 5% | Reduction factor - 40% by volume | | | |
| g $H_2O$ for PEI mix | 100 | Titanate (g) | | 0.1125 | | | | |
| g of $H_2O$ for PAA mix | 292.8 | | | | Computation of ppm | | | |
| g $H_2O$ in bulk PAA | 1.05 | Photocatalyst (% wbcm) | | 10% | 2.25 | X | X = 3.21k ppm | |
| Total Fluid | 1169.25 | Photocatalyst (g) | | 0.18 | 701.55 | 1000 | | |

The antimicrobial composition that creates the PEC set forth in Table 8 comprises two cationic polymers (i.e., polyDADMAC and PEI), an anionic polymer (PAAS), a titanate, $TiO_2$ particles (photocatalyst), and water as the carrier. Alcohol is not required for the creation of the PEC. Following the formation of the PEC, a certain percentage of the water is replaced with alcohol. When the composition is used as a spray on disinfectant, the alcohol helps kill bacteria. The alcohol also helps the composition dry faster to form a residual self-sanitizing film. This replacement of water with alcohol can range from 5% alcohol to 90% alcohol, preferably from 35% to 70%.

Example 2

This example demonstrates the future antimicrobial protection against gram positive methicillin-resistant *Staphylococcus aureus* (MRSA) bacteria and gram negative *Escherichia coli* (ATCC 8739) bacteria exhibited by an antimicrobial composition in accordance with an embodiment of the invention.

Disinfecting compositions were prepared comprising either 250 kDa pDADMAC or ultra-high molecular weight (1,000,000 g/mol) pDADMAC, a water-methanol mixture, titanate, and functionalized $TiO_2$ particles as set forth in Table 9. The kill rates and times reported are after inoculation of a 7-day-old film with the bacteria. The bacteria testing was conducted by an independent test laboratory, BioSan Laboratories, Inc. (Warren, Mich.), and the results for the 4.8K ppm film are set forth in Table 10. A simulated EPA durability test used herein consists of the requisite 12 alternating wet and dry wipes with a prescribed weight. Recovered organisms from each sample were measured after 5 minutes. The results are set forth in Table 10, row 4.

TABLE 9

| | Percent for Film (ppm) | |
|---|---|---|
| | 4.8k ppm | 3.2k ppm |
| Total Fluid (80% $H_2O$ and 20% methanol) | 500 ml | 750 ml |
| grams of PolyDADMAC, 40% solids | 6 | 6 |
| Solids in grams | 2.4 | 2.4 |
| grams titanate (LICA ™ 09), 5% weight by monomer | 0.12 | 0.12 |

TABLE 9-continued

| | Percent for Film (ppm) | |
|---|---|---|
| | 4.8k ppm | 3.2k ppm |
| grams of functionalized $TiO_2$, 10% weight by monomer | 0.24 | 0.24 |

TABLE 10

| Bacteria Tested | Material and/or Special Test Conditions | Initial Log | % Killed in 5 Minutes |
|---|---|---|---|
| MRSA (ATCC 33591) | ultra-high MW pDADMAC only | $5.93 \times 10^5$ | 99.83% |
| MRSA (ATCC 33591) | 250,000 g/mol MW pDADMAC only | $3.25 \times 10^4$ | 89.4% |
| *Escherichia coli* (ATCC 8739) | ultra-high MW pDADMAC only | $2.50 \times 10^5$ | 99.54% |
| *Escherichia coli* (ATCC 8739) | ultra-high MW pDADMAC only after EPA durability test | $3.40 \times 10^5$ | 99.70% |

As is apparent from the results set forth in Table 10, the ultra-high molecular weight pDADMAC is very effective at preventing future growth of both gram-positive (MRSA) and gram-negative (*E. coli*) bacteria, killing greater than 99.5% in 5 minutes. In addition, these results were measured after a period of 7 days demonstrating that the antimicrobial residual self-sanitizing film is continually killing at this efficient level. Furthermore, the ultra-high molecular weight polyDADMAC is equally effective at killing gram-negative (*E. coli*) bacteria after the EPA durability test. Thus, the antimicrobial residual self-sanitizing film does not easily wipe off of the surface.

Example 3

This example demonstrates the future antimicrobial protection against influenza A (H1N1) (ATCC CCL-34) enveloped virus and MS2 (ATCC 15597-B1) non-enveloped virus exhibited by an antimicrobial composition in accordance with an embodiment of the invention.

Disinfecting compositions comprising pDADMAC and/or PEI, a titanate, and optionally functionalized $TiO_2$ in a water-methanol mixture were prepared in accordance with either Table 8, 9, or 11. The kill rates and times reported are after inoculation of a 7-day-old film with the virus. The virus testing was conducted by an independent test laboratory, Antimicrobial Test Laboratories (Round Rock, Tex.), and the results set forth in Table 12.

addition of 33% PEI. Without PEI, 82.3% are killed within 30 minutes, but with 33% PEI 95% are killed within 30 minutes. Furthermore, Table 12 demonstrates that an antimicrobial composition comprising pDADMAC and $TiO_2$ only kills 82.3% of the non-enveloped MS2 virus within 30 minutes of contact, this increased to 97.8% after 24 hours.

Example 4

This example demonstrates the future antimicrobial protection against spore generating *Clostridium difficile* (ATCC 43598) bacteria exhibited by an antimicrobial composition in accordance with an embodiment of the invention.

An antimicrobial composition was prepared comprising ultra-high molecular weight pDADMAC, a titanate, and functionalized $TiO_2$ in a water-methanol mixture as set forth in Table 9. The kill rates and times reported are after inoculation of a 7-day-old film with the bacteria. The bacteria testing was conducted by an independent test laboratory, Antimicrobial Test Laboratories (Round Rock, Tex.), and the results set forth in Table 13.

TABLE 11

| Components | Mass (g) | % Solids | Solids (g) | $H_2O$ (g) | Cationic Solids in $H_2O$ (g) | Anionic Solids in $H_2O$ (g) | % of total fluid | Charged monomer Ratio of $n^-/n^+$ |
|---|---|---|---|---|---|---|---|---|
| pDADMAC | 0 | 40% | 0 | 0 | 0 | | 0.00% | 0.2625 |
| PEI | 0.8 | 100% | 0.8 | 300.00 | 0.8 | | 0.20% | |
| PAAS | 0.7 | 30% | 0.21 | 100.49 | | 0.21 | | |
| g $H_2O$ for pDADMAC mix | n/a | | Total Cationic Polymer | | 0.8 | 0.21 | Total Anionic Polymer | |
| g $H_2O$ in bulk pDADMAC | 0 | Titanate (% wbtm) | 5% | | Reduction factor - 30% by volume | | | |
| g $H_2O$ for PEI mix | 300 | Titanate (g) | 0.0505 | | | | | |
| g of $H_2O$ for PAA mix | 100 | | | | Computation of ppm | | | |
| g $H_2O$ in bulk PAA | 0.49 | Photocatalyst (% wbcm) | 0% | 1.01 | X | | X = 3.6k ppm | |
| Total Fluid | 400.49 | Photocatalyst (g) | 0 | 280.34 | 1000 | | | |

TABLE 12

| Virus Tested | Material and/or Special Test Conditions | Initial Log | % Killed 5 Min | % Killed 10 Min | % Killed 30 Min | % Killed 60 Min | % Killed 24 Hrs |
|---|---|---|---|---|---|---|---|
| influenza A (H1NI) | ultra high MW pDADMAC/$TiO_2$ (Table 9) | $4.8 \times 10^4$ | | | 98.2% | 99.0% | |
| MS2 (ATCC 15597-B1) | ultra high MW pDADMAC/$TiO_2$ (Table 9) | $5.5 \times 10^4$ | | | 82.3% | | 97.8% |
| MS2 (ATCC 15597-B1) | PEI Only (Table 11) | $2.4 \times 10^4$ | 97.4% | 98.3% | 99.1% | | |
| MS2 (ATCC 15597-B1) | 0.33 PEI/0.66 pDADMAC/$TiO_2$ (Table 8) | $1.9 \times 10^4$ | 87.5% | | 95.0% | | |

As is apparent from the results set forth in Table 12, antimicrobial compositions comprising pDADMAC and $TiO_2$ lyse 98.2% of a log 4 population of influenza A (H1NI) virus within 30 minutes of contact and 99% within 60 minutes. In addition, antimicrobial compositions comprising PEI kill 97.4% of a log 4 population of the non-enveloped virus MS2 within 5 minutes, and 99% within 30 minutes. Table 12 also demonstrates that disinfecting compositions comprising polyDADMAC, $TiO_2$, and PEI become more antiviral, particularly against non-enveloped MS2, with the

TABLE 13

| C. diff Tested | Material and/or Special Test Conditions | Initial Log | % Killed in 8 hr |
|---|---|---|---|
| ATC #43598 | ultra-high MW pDADMAC/$TiO_2$ | $6.75 \times 10^5$ | 98% |

As is apparent from the results set forth in Table 13, an antimicrobial composition comprising ultra-high molecular weight pDADMAC and TiO$_2$ kills 98% of a log 5 population of *Clostridium difficile* (ATCC 43598) bacteria in 8 hours.

Example 5

This example demonstrates the future antimicrobial protection against *Aspergillas brasliensis* fungus exhibited by an antimicrobial composition in accordance with an embodiment of the invention.

An antimicrobial composition comprising ultra-high molecular weight pDADMAC, a titanate, and functionalized TiO$_2$ in a water-methanol mixture was prepared using the formulation set forth in Table 9. The kill rates and times reported are after inoculation of a 7-day-old film with the fungus. The fungus testing was conducted by independent test laboratory, BioSan Laboratories, Inc. (Warren, Mich.) and the results set forth in Table 14.

TABLE 14

| Fungus Tested | Material and/or Special Test Conditions | Initial Log | % Killed in 8 hr |
|---|---|---|---|
| *Aspergillas brasliensis* | ultra-high MW pDADMAC/TiO$_2$ | 2.15 × 10$^4$ | 86% |

As is apparent from the results set forth in Table 14, an antimicrobial composition comprising ultra-high molecular weight pDADMAC, a titanate, and TiO$_2$ kills 86% of a log 4 population of *Aspergillas brasliensis* fungus in 8 hours.

Example 6

This example demonstrates the future antimicrobial protection against gram positive methicillin-resistant *Staphylococcus aureus* (MRSA) bacteria exhibited by an antimicrobial composition in accordance with an embodiment of the invention.

Disinfecting compositions were prepared in accordance with the components set forth in Table 9 except that no titanium dioxide was present. A simulated EPA durability test used herein consists of the requisite 12 alternating wet and dry wipes with a prescribed weight. Recovered organisms from each sample were measured after 5 minutes. The results are set forth in Table 15.

TABLE 15

| Sample | Methicillin-resistant *Staphylococcus aureus* (MRSA) ATCC 33591 cfu/sample* | % Reduction | Antimicrobial Activity |
|---|---|---|---|
| Untreated control | 1.19 × 10$^4$ | n/a | n/a |
| 3.2k ppm | <10 | >99.92% | >3.08 |
| 4.8k ppm | <10 | >99.92% | >3.08 |

*cfu/sample—colony forming units per sample recovered

This example demonstrates the "kill later" antimicrobial protection against MRSA exhibited by a film formed by an antimicrobial composition containing polyDADMAC, a titanate, and a carrier.

Example 7

This example demonstrates the antimicrobial activity exhibited by a composition comprising pDADMAC and a carrier.

Antimicrobial compositions were prepared comprising either low molecular weight polyDADMAC (250,000 g/mol) or ultra-high molecular weight (1,000,000 g/mol) polyDADMAC in a water-methanol (80/20) mixture. The composition was coated onto a clear glass slide that was allowed to dry to form a film. The killing power of the polyDADMAC film was tested against Methicillin-resistant *Staphylococcus aureus* (MRSA). Recovered organisms from each sample were measured after 5 minutes. The results are set forth in Table 16.

TABLE 16

| Molecular Weight (g/mol) | Sample | methicillin-resistant *Staphylococcus aureus* (MRSA) ATCC 33591 cfu/sample* | % Reduction | Antimicrobial Activity |
|---|---|---|---|---|
| Low (250,000) | Untreated control 9690 | 1.95 × 10$^7$ 1.64 × 10$^5$ | n/a 99.16% | n/a 2.08 |
| Ultra-High (1,000,000) | Untreated control 9855 | 8.88 × 10$^6$ 1.5 × 10$^1$ | n/a >99.99% | n/a 5.77 |

*cfu/sample—colony forming units per sample recovered

It was unexpectedly discovered that a film created with an ultra-high molecular weight polyDADMAC is considerably more effective than a lower molecular weight (250,000 g/mol) at killing gram-positive and gram-negative bacteria. As seen in Table 16, after 5 minutes of exposure to a log 7 MRSA population, the 250,000 g/mol MW film only provides an antimicrobial activity of 2.08. In comparison, a 1,000,000 g/mol MW film created an antimicrobial activity of 5.7, i.e., more than double, using the same amount of polymer in each case. It is believed that the difference in the kill rate of the lower molecular weight polyDADMAC compared to the higher molecular weight polyDADMAC is likely due to the differences in film formation rather than differences in charge density.

Example 8

This example demonstrates providing a residual self-sanitizing film on a textile with an antimicrobial composition in an embodiment of the invention.

An antimicrobial composition in the form of a PEC comprising 6,000 ppm pDADMAC, 1,500 ppm polyacrylic acid, 400 ppm titanate, and 0.1% w/w functionalized TiO$_2$ particles was prepared. The composition was applied in a rinse cycle to a cloth and then was tested for antimicrobial resistance using the American Association of Textile Chemists and Colorists (AATCC) test method 100, which is designed to assess the performance of antimicrobial finishes on textiles. The test demonstrated that the polymer-based composition was able to lysis 99.58% of a log 4 MRSA population on a cloth after 4 hours (Table 17). While AATCC does not specify a standard, a similar test method, ISO 20743, recommends a 2-$Log_{10}$ or 99% reduction.

TABLE 17

| Test Microorganism | Contact Time | Carrier Type | LUX Exposure | CFU/Carrier | Percent Reduction Compared to control at Time Zero | $Log_{10}$ Reduction Compared to Control at Time Zero |
|---|---|---|---|---|---|---|
| S. aureus ATCC 33591 (MRSA) | Time zero | Microchem control | n/a | 3.95E+04 | n/a | n/a |
| | 4 hours | Control 0 wash cycles | ~1500 lux | 5.70E+04 1.65E+02 | 99.58% | 2.38 |

A second antimicrobial composition comprising 4000 ppm PEI, 2000 ppm poly(acrylamide-co-diallyldimethylammonium chloride), and 25 ppm carboxylated branched PEI in a carrier was prepared and had a pH of about 6. The composition was applied in a rinse cycle to a cloth and then tested for antimicrobial resistance under the same conditions above. The results are summarized in Table 18.

TABLE 18

| Test Microorganism | Carrier Type | Contact Time | CFU/Carrier | Percent Reduction Compared to control at Time Zero | $Log_{10}$ Reduction Compared to Control at Time Zero |
|---|---|---|---|---|---|
| S. aureus ATCC 33592 (MRSA) | Microchem control | Time zero | 4.10E+05 | n/a | n/a |
| | Antimicrobial composition | 10 min | 9.10E+04 | 77.8% | 0.65 |
| | | 20 min | 6.15E+03 | 98.5% | 1.82 |
| | | 30 min | 3.11E+03 | 99.2% | 2.12 |

Example 9

This example demonstrates the antimicrobial protection against *E. coli* exhibited by an antimicrobial composition containing titanate.

A composition comprising titanate in water was applied to a glass slide. The coated slide was allowed to set for 5 days, and then the slide was inoculated with a log 6 *E. coli* population. The pure titanate film resulted in an 88.72% kill after 24 hours, as seen in Table 19.

TABLE 19

| Sample | *Escherichia coli* ATCC 8739 cfu/sample* | % Reduction | Antimicrobial Activity |
|---|---|---|---|
| Untreated control | >5.08 × 10⁶ | n/a | n/a |
| 9853 | 5.73 × 10⁵ | >88.72% | >0.95 |

*cfu/sample—colony forming units per sample recovered

Example 10

This example demonstrates the antimicrobial activity of a hand sanitizer composition in an embodiment of the invention.

At room temperature, 4000 ppm of linear PEI in water was stirred vigorously to create a PEI dispersion. Under vigorous stirring, the PEI in the dispersion was then protonated with citric acid, thereby bringing the pH to 6 and resulting in a clear liquid. The clear liquid was then brought to a temperature of 70° C. Ethanol and 1,2-propanediol were then drizzled in so as to maintain the temperature of the clear liquid at 65° C. The clear mixture was taken off the heat to avoid excessive alcohol evaporation and then stirred for a minimum of 4 hours while covered. The resulting miscible blend comprised 4000 pm non-chemically modified, linear PEI, 72% ethanol, 5% 1,2-propanediol, 0.25% by weight citric acid, and the balance water.

The activity of the hand sanitizer composition against non-enveloped viruses was in accordance with ASTM E 1052-96 (2002) ("Standard Test Method to Assess the Activity of Microbicides against Viruses in Suspension"). Using this test the hand sanitizer formulation inactivated MS2 (a surrogate for non-enveloped viruses) with a 99.9% (log 3) reduction within 60 seconds of contact. The activity of the hand sanitizer composition against MRSA (gram positive bacteria) and *E. coli* (gram negative bacteria) was in accordance with ASTM E 2315. The hand sanitizer composition inactivated both bacteria with a 99.999% (log 5) reduction within 30 seconds of contact. The results of these tests are summarized in Table 20.

TABLE 20

| Pathogen | Suspension Test | Percent Killed Within 30 Seconds of Contact | Percent Killed Within 60 Seconds of Contact |
|---|---|---|---|
| MS2 (surrogate for non-enveloped virus) | ASTM E2315 | 99.7% | 99.9% |
| MRSA | ASTM E-1052-96 | 99.999% | 99.999% |
| E. Coli | ASTM E-1052-96 | 99.999% | 99.999% |

Example 11

This example demonstrates the synthesis of functionalized TiO$_2$ particles in an embodiment of the invention.

TiO$_2$ particles were functionalized using the following method. Starting with 1 g of tungsten-doped, 20 nm liquid-synthesized TiO$_2$, 5 g urea was added, and the mixture was calcined for 40 min at 400° C. to yield NTiO$_2$. The NTiO$_2$ was then ground to a fine powder, to which was added 10 g of milling balls for every gram of NTiO$_2$ plus 10% urea. The mixture was milled for 30 min at 300 rpm. After 30 min, 200 mL of water was added, and the mixture was milled an additional 5 min. The milled mixture was then subjected to 160 W UV light. After 1 hour, the mixture was decanted and centrifuged and 0.5 mM dye was added in the dark. The mixture was again decanted and centrifuged, after which water was added once more.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An antimicrobial composition consisting of
cationic, non-chemically modified, linear polyethylenimine (PEI),
a polydiallyldialkylammonium salt,
a carrier selected from ethanol, n-propanol, iso-propanol, n-butanol, sec-butanol, and t-butanol, water, and a combination thereof, and
optionally one or more components selected from the group consisting of
(a) an adhesion promoter,
(b) a non-electrolyte polymer selected from the group consisting of a polyacrylamide, a polyamine, a polyamidoamine, polyethylene glycol, polyvinyl pyrrolidone, polyvinyl alcohol, a polyacrylate, and any combination thereof,
(c) a polyacid selected from the group consisting of isocitric acid, aconitic acid, propane-1,2,3-tricarboxylic acid, hemimelitic acid, trimellitic acid, trimesic acid, prehnitic acid, meallanophanic acid, pyromellitic aicd, benzenepentacarboxylic acid, mellitic acid, ethylenediamine-N,N'-dimalonic acid (EDDM), 2,2'-azanediyldisuccinic acid, 2,2'-oxydisuccinic acid (ODS), ethylenediaminedisuccinic acid (EDDS), diethylenetriaminepentaacetic acid (DTPA), ethylene diamine tetraacetic acid (EDTA), 2,2'4((1,2-dicarboxyethyl)azanediyl)bis(ethane-2,1-diyl))bis(oxy))disuccinic acid, and a combination thereof,
(d) a proton donor selected from the group consisting of nitric acid, phosphoric acid, phosphonic acid, boric acid, sulfuric acid, adipic acid, benzene 1,3,5 tricarboxylic acid, chlorosuccinic acid, cholinechloride, cis-aconitic acid, citramalic acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, maleic acid, malic acid, malonic acid, nitrilotriacetic acid, oxalacetic acid, oxalic acid, phytic acid, p-toluenesulfonic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane, 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxo-glutaric acid, dl-glyceric acid, 2,5 furandicarboxylic acid, and a combination thereof,
(e) propylene glycol,
(f) a thickening agent,
(g) a humectant,
(h) an essential oil,
(i) a fruit extract,
(j) a fragrance, and
(k) a dye,
wherein the antimicrobial composition is in accordance with one or more of the following tests:
(i) a germicidal spray test according to American Society for Testing and Materials (ASTM) international method E1153 that meets the EPA requirement of log 3 reduction for viruses and a log 5 reduction for bacteria,
(ii) a film formed from the composition kills
(ii-a) at least 95% of log 5 population of a gram positive or gram negative bacteria in 30 minutes,
(ii-b) at least 95% of log 4 population of an enveloped virus within 30 minutes of contact of contact, (ii-c) at least 95% of a non-enveloped virus within 30 minutes of contact, and/or (ii-d) at least 94% of a log 4 population of *Clostridium difficile* bacteria within 24 hours of contact, in accordance with Japanese Industrial Standard (JIS) Z 2801 (2006) test for antimicrobial activity, or a modified version of such test, and (iii) a durability test selected from either (v-a) a film formed from the composition kills at least 99.9% of gram-positive bacteria and gram-negative bacteria according to Environmental Protection Agency (EPA) Protocol #01-1A residual self-sanitizing activity test, or (v-b) waiting 7 days after film formation, a film formed from the composition kills at least 95% of gram-positive bacteria and gram-negative bacteria, or enveloped and non-enveloped viruses according to a modified version of Protocol #01-1A residual self-sanitizing activity test.

2. The antimicrobial composition of claim 1, wherein the polydiallyldialkylammonium salt is a polydiallyldialkylammonium halide, a polydiallyldialkylammonium sulfate, or polydiallyldialkylammonium phosphate.

3. The antimicrobial composition of claim 1, wherein the polydiallyldialkylammonium salt is polydiallyldimethylammonium chloride (polyDADMAC).

4. The antimicrobial composition of claim 1, wherein a polyacid is present in the composition.

5. The antimicrobial composition of claim 1, wherein at least one adhesion promoter is present in the composition and is selected from a titanate, branched or linear PEI having carboxylic acid groups, a silane compound, cationic block copolymers, and a polymer comprising at least one acyl group, carboxylic acid group, or carboxylic acid derivative, and a combination thereof.

6. The antimicrobial composition of claim 5, wherein the at least one adhesion promoter is branched PEI having carboxylic acid groups.

7. The antimicrobial composition of claim 1, wherein one or more non-electrolyte polymers are present in the composition.

8. The antimicrobial composition of claim 7, wherein the one or more non-electrolyte polymers comprises polyvinyl pyrrolidone.

9. The antimicrobial composition of claim 1, wherein the composition consists of cationic, non-chemically modified linear PEI, polyDADMAC, optionally branched PEI having carboxylic acid groups, optionally polyvinyl pyrrolidone, and the carrier is water, ethanol, or a combination thereof.

10. A method of killing microbes on a surface comprising applying to the surface the antimicrobial composition of claim 1.

11. The method of claim 10, wherein the carrier evaporates to leave a residual self-sanitizing film on the surface.

12. The method of claim 11, wherein the surface comprises a textile.

13. The method of claim 11, wherein the surface is part of a filter.

14. The method of claim 10, wherein the composition consists of cationic, non-chemically modified, linear PEI, polydiallyldimethylammonium chloride (polyDADMAC), a carrier selected from ethanol, n-propanol, iso-propanol, n-butanol, sec-butanol, and t-butanol, water, and a combination thereof, and optionally one or more components selected from the group consisting of (a) an adhesion promoter, (b) a non-electrolyte polymer selected from the group consisting of a polyacrylamide, a polyamine, a polyamidoamine, polyethylene glycol, polyvinyl pyrrolidone, polyvinyl alcohol, a polyacrylate, and any combination thereof, (c) a polyacid selected from the group consisting of isocitric acid, aconitic acid, propane-1,2,3-tricarboxylic acid, hemimelitic acid, trimellitic acid, trimesic acid, prehnitic acid, meallanophanic acid, pyromellitic aicd, benzenepentacarboxylic acid, mellitic acid, ethylenediamine-N,N'-dimalonic acid (EDDM), 2,2'-azanediyldisuccinic acid, 2,2'-oxydisuccinic acid (ODS), ethylenediaminedisuccinic acid (EDDS), diethylenetriaminepentaacetic acid (DTPA), ethylene diamine tetraacetic acid (EDTA), 2,2'4((1,2-dicarboxyethyl)azanediyl)bis(ethane-2,1-diyl))bis(oxy))disuccinic acid, and a combination thereof, (d) a proton donor selected from the group consisting of nitric acid, phosphoric acid, phosphonic acid, boric acid, sulfuric acid, adipic acid, benzene 1,3,5 tricarboxylic acid, chlorosuccinic acid, cholinechloride, cis-aconitic acid, citramalic acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, maleic acid, malic acid, malonic acid, nitrilotriacetic acid, oxalacetic acid, oxalic acid, phytic acid, p-toluenesulfonic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane, 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxo-glutaric acid, dl-glyceric acid, 2,5 furandicarboxylic acid, and a combination thereof, (e) propylene glycol, (f) a thickening agent, (g) a humectant, (h) an essential oil, (i) a fruit extract, (j) a fragrance, and (k) a dye.

15. The method of claim 10, wherein the composition consists of cationic, non-chemically modified linear PEI, polyDADMAC, optionally branched PEI having carboxylic acid groups, optionally polyvinyl pyrrolidone, and the carrier is water, ethanol, or a combination thereof.

16. An antimicrobial composition comprising (a) a polymeric antimicrobial agent consisting of cationic, non-chemically modified, linear polyethylenimine (PEI), and a polydiallyldialkylammonium salt, (b) optionally a non-electrolyte polymer selected from a polyacrylamide, a polyamine, a polyamidoamine, polyethylene glycol, polyvinyl pyrrolidone, polyvinyl alcohol, a polyacrylate, and any combination thereof, (c) optionally at least one adhesion promoter, and (d) a carrier selected from ethanol, n-propanol, iso-propanol, n-butanol, sec-butanol, and t-butanol, water, and a combination thereof, wherein
the antimicrobial composition does not comprise a non-polymer germicidal compound, an antimicrobial metal, an anionic polymer, or a polymeric antimicrobial agent other than (a),
and
the antimicrobial composition is in accordance with one or more of the following tests:
(i) a germicidal spray test according to American Society for Testing and Materials (ASTM) international method E1153 that meets the EPA requirement of log 3 reduction for viruses and a log 5 reduction for bacteria,
(ii) a film formed from the composition kills
   (ii-a) at least 95% of log 5 population of a gram positive or gram negative bacteria in 30 minutes,
   (ii-b) at least 95% of log 4 population of an enveloped virus within 30 minutes of contact of contact,
   (ii-c) at least 95% of a non-enveloped virus within 30 minutes of contact, and/or
   (ii-d) at least 94% of a log 4 population of *Clostridium difficile* bacteria within 24 hours of contact,
in accordance with Japanese Industrial Standard (JIS) Z 2801 (2006) test for antimicrobial activity, or a modified version of such test, and
(iii) a durability test selected from either (v-a) a film formed from the composition kills at least 99.9% of gram-positive bacteria and gram-negative bacteria according to Environmental Protection Agency (EPA) Protocol #01-1A residual self-sanitizing activity test, or (v-b) waiting 7 days after film formation, a film formed from the composition kills at least 95% of gram-positive bacteria and gram-negative bacteria, or enveloped and non-enveloped viruses according to a modified version of Protocol #01-1A residual self-sanitizing activity test.

17. The antimicrobial composition of claim 16, wherein the polydiallyldialkylammonium salt is polydiallyldimethylammonium chloride (polyDADMAC).

18. The antimicrobial composition of claim 16, wherein the composition further comprises at least one adhesion promoter selected from a titanate, branched or linear PEI having carboxylic acid groups, a silane compound, cationic block copolymers, and a polymer comprising at least one acyl group, carboxylic acid group, or carboxylic acid derivative, and a combination thereof.

19. The antimicrobial composition of claim 16, wherein the composition further comprises one or more non-electrolyte polymers.

20. A method of killing microbes on a surface comprising applying to the surface the antimicrobial composition of claim 16.

21. The antimicrobial composition of claim 1, wherein the cationic, non-chemically modified, linear polyethylenimine comprises iminium acetate.

22. The antimicrobial composition of claim 16, wherein the cationic, non-chemically modified, linear polyethylenimine comprises iminium acetate.

23. The antimicrobial composition of claim 1, wherein the carrier is ethanol or a combination of ethanol and water.

24. The antimicrobial composition of claim 16, wherein the carrier is ethanol or a combination of ethanol and water.

25. The antimicrobial composition of claim 1, wherein the cationic, non-chemically modified, linear PEI and polydiallyldialkylammonium salt form a crystalline miscible blend in the carrier.

26. The antimicrobial composition of claim 16, wherein the cationic, non-chemically modified, linear PEI and polydiallyldialkylammonium salt form a crystalline miscible blend in the carrier.

27. The antimicrobial composition of claim 1, wherein the composition has a pH between 3-7.

28. The antimicrobial composition of claim 16, wherein the composition has a pH between 3-7.

* * * * *